US009796659B2

(12) United States Patent
Albrecht et al.

(10) Patent No.: US 9,796,659 B2
(45) Date of Patent: Oct. 24, 2017

(54) DERIVATIVES OF POLYHYDROXY COMPOUNDS

(71) Applicant: RATIOPHARM GMBH, Ulm (DE)

(72) Inventors: Wolfgang Albrecht, Ulm (DE); Frank Lehmann, Neu-Ulm (DE); Roland Selig, Ulm (DE); Sebastian Rabe, Neu-Ulm (DE); Annemarie Maier, Biberach (DE); Richard Guserle, Kötz (DE)

(73) Assignee: ratiopharm GmbH, Ulm (DE)

( * ) Notice: Subject to any disclaimer, the term of this patent is extended or adjusted under 35 U.S.C. 154(b) by 0 days.

(21) Appl. No.: 15/112,683

(22) PCT Filed: Feb. 27, 2015

(86) PCT No.: PCT/EP2015/054191
§ 371 (c)(1),
(2) Date: Jul. 19, 2016

(87) PCT Pub. No.: WO2015/128488
PCT Pub. Date: Sep. 3, 2015

(65) Prior Publication Data
US 2017/0001945 A1    Jan. 5, 2017

Related U.S. Application Data
(60) Provisional application No. 61/945,363, filed on Feb. 27, 2014.

(30) Foreign Application Priority Data
Apr. 2, 2014   (EP) ..................... 14163150
Jun. 26, 2014  (EP) ..................... 14174057

(51) Int. Cl.
| | |
|---|---|
| *C07C 69/60* | (2006.01) |
| *C07C 229/22* | (2006.01) |
| *A61K 9/00* | (2006.01) |
| *A61K 31/225* | (2006.01) |
| *C07C 69/604* | (2006.01) |

(52) U.S. Cl.
CPC ............ *C07C 69/60* (2013.01); *A61K 9/0053* (2013.01); *A61K 31/225* (2013.01); *C07C 69/604* (2013.01); *C07C 229/22* (2013.01)

(58) Field of Classification Search
None
See application file for complete search history.

(56) References Cited

PUBLICATIONS

Database Caplus Chemical Abstracts Service, Columbus, Ohio, US; Database Accession No. 2010:604425, Abstract of Chen et al., Jiangsu Keji Daxue Xuebao, Ziran Kexueban (2009), 23(6), 553-556.*
PCT/EP2015/054191, Int'l Preliminary Report on Patentability & Written Opinion of the ISA, dated Mar. 30, 2016.
PCT/EP2015/054191, Int'l Search Report, dated May 8, 2015.

* cited by examiner

*Primary Examiner* — Karl J Puttlitz
(74) *Attorney, Agent, or Firm* — Milstein Zhang & Wu LLC

(57) ABSTRACT

The present invention relates to novel compounds, e.g. for use as a medicament. In particular, the present invention relates to novel prodrugs of monomethyl fumarate (MMF) suitable as a medicament, preferably in the treatment and/or prevention of systemic diseases, autoimmune diseases, inflammatory diseases, for example multiple sclerosis and psoriasis.

8 Claims, 3 Drawing Sheets

DERIVATIVES OF POLYHYDROXY COMPOUNDS

The present invention relates to novel compounds, e.g. for use as a medicament. In particular, the present invention relates to novel prodrugs of monomethyl fumarate (MMF) suitable as a medicament, preferably in the treatment and/or prevention of systemic diseases, autoimmune diseases, and/or inflammatory diseases, for example multiple sclerosis and psoriasis. Further, the invention relates to a pharmaceutical composition comprising the novel compounds.

BACKGROUND OF THE INVENTION

Dimethyl fumarate (DMF) is an oral therapeutic agent which is reported to reduce the rejection often occurring in connection with an organ transplantation (host versus graft reaction). Further, DMF is approved to be suitable as medicament for the treatment or prevention of a variety of diseases. For example, DMF is proposed in the treatment of autoimmune diseases such as multiple sclerosis. Further, DMF is suggested to be a suitable active pharmaceutical agent in the treatment of psoriasis. DMF is characterized by the following chemical Formula (1):

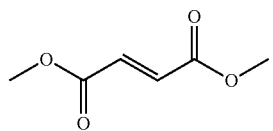

Formula (1)

When taken orally DMF is reported to be hydrolyzed for example by the acidic ambience of the stomach or by esterases in the intestine to monomethyl fumarate (MMF). MMF can be regarded as a metabolite of DMF and can be characterized by the following chemical Formula (2):

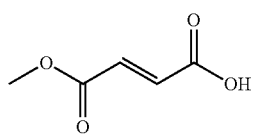

Formula (2)

The mechanisms of action of DMF or its metabolite MMF is reported to include inhibition of cytokine-induced nuclear translocation of the nuclear factor kappa (NF-κB), apoptosis of stimulated T cells, and increased production of the $T_h2$ cytokines IL-4 and IL-5 in stimulated T cells, whereas generation of the $T_h1$ cytokine interferon gamma (IFN-γ) is supposed to remain unaffected. DMF is described to activate the transcription factor Nrf2 (nuclear factor erythroid 2-related factor 2), which binds to antioxidant response elements in the promoters of protective genes such as NADPH-quinone-oxidoreductase-1 (NQO1) and heme-oxygenase-1. Thus, this ultimately raises the levels of the important intracellular antioxidant glutathione (cf. Albrecht P. et al., Journal of Neuroinflammation 2012, 9:163).

Further, it is alleged that the treatment of animals or primary cultures of CNS cells with DMF or MMF resulted in increased nuclear levels of active Nrf2, with subsequent up-regulation of canonical antioxidant target genes. DMF or MMF treatment increased cellular redox potential, glutathione, ATP levels, and mitochondrial membrane potential in a concentration-dependent manner. Treating astrocytes or neurons with DMF or MMF also significantly improved cell viability after toxic oxidative challenge in a concentration-dependent manner. This effect on viability was lost in cells that had eliminated or reduced Nrf2. These data suggest that DMF and MMF are cytoprotective for neurons and astrocytes against oxidative stress-induced cellular injury and loss, potentially via up-regulation of an Nrf2-dependent antioxidant response. Thus, in summary, it is indicated that in vivo DMF and MMF show about the same the efficacy, in particular on the transcription factor Nrf2.

As mentioned above, when taken orally DMF is rather rapidly hydrolyzed for example by the acidic ambience of the stomach or by esterases in the intestine to monomethyl fumarate (MMF). Thus, significant amounts of MMF are released within a short period of time. Such a rapid hydrolyzation in principle was expected to provide a high level of MMF in the plasma within a short period of time. However, it has been found that a high MMF plasma level might not be achievable. A reason might be that the organism may not be capable of transferring the complete amount of MMF to the sites of the body where the pharmacological action takes place.

Additionally, it is reported that DMF has to be administered in quite high amounts and that the pharmaceutically active agent often shows undesirable side effects such as flush and especially symptoms related to the gastrointestinal tract such as irritation of the stomach and diarrhoea.

Consequently, there is still a need for new medicaments, preferably for use in the treatment and/or prevention of systemic diseases, autoimmune diseases, inflammatory diseases, for example multiple sclerosis and psoriasis. The medicaments should be capable of being applied in appropriate doses and should not cause significant undesired side effects.

Hence, it was an object of the present invention to overcome the drawbacks of the above-mentioned market drug substance DMF.

It was an object to develop a compound to be used as a medicament for the above-mentioned diseases wherein said compound shows advantageous pharmacokinetic properties.

Moreover, compounds should be provided which are hydrolysed to MMF more slowly than DMF in the human body (or under respective in-vitro conditions).

Further, the compounds should preferably cause few undesirable side effects.

Additionally, it was an object of the present invention to provide compounds which can be used in the treatment of the early phase of an autoimmune disease, in particular of multiple sclerosis, such that the progress of the disease can be delayed.

SUMMARY OF THE INVENTION

According to the present invention, the above objectives are achieved by the specific compounds described herein by Formula (I), Formula (II) or Formula (IIa) with the proviso that the compound is not represented by Formula (III), and by a compound described herein by Formula (VIII). Said compounds can be used as a medicament for the treatment and/or prevention of systemic diseases, autoimmune diseases, and/or inflammatory diseases, for example multiple sclerosis and psoriasis.

The compounds of the invention can be regarded as MMF prodrugs. Generally, a prodrug can be regarded as a substance that is administered to a subject (preferably human) in a pharmacologically inactive or pharmacologically less than fully active form, and is subsequently converted in the body of the subject to an active drug, preferably through metabolic processes occurring in the body of the subject. In other words, a prodrug usually serves as a type of 'precursor' to the intended drug.

Thus, the subject of the present invention is a compound according to one of Formula (I), (II), (IIa) and (VIII). That means, the subject of the present invention is a compound according to one of Formula (I), Formula (II) or Formula (IIa)

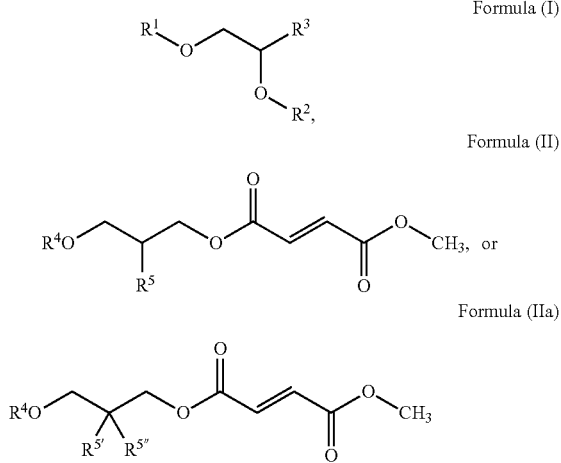

Formula (I)

Formula (II)

Formula (IIa)

wherein $R^1$, $R^2$ are hydrogen or trans —CO—CH=CH—COOCH$_3$ and wherein at least one of $R^1$ and $R^2$ is trans —CO—CH=CH—COOCH$_3$, and
$R^3$, $R^4$ and $R^5$ are each independently an organic residue, $R^{5'}$ and $R^{5''}$ taken together are =O, =S or =NR$^{100}$, wherein $R^{100}$ is hydrogen or alkyl with 1 to 4 carbon atoms,
or a pharmaceutically acceptable salt, hydrate, solvate, polymorph, enantiomer, diastereomer or mixtures thereof,
with the proviso that the compound is not represented by Formula (III)

Formula (III)

or a compound according to Formula (VIII)

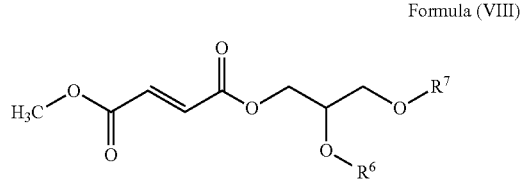

Formula (VIII)

wherein one of $R^6$ and $R^7$ is —CO—CH$_2$CH(OH)CH$_2$N$^\oplus$(CH$_3$)$_3$X$^\ominus$ or —CO—CH$_2$CH(OCOCH$_3$)CH$_2$N$^\oplus$(CH$_3$)$_3$X$^\ominus$ and the other one of $R^6$ and $R^7$ is hydrogen or trans —CO—CH=CH—COOCH$_3$, and wherein X$^\ominus$ is a pharmaceutically acceptable anion,
or a pharmaceutically acceptable hydrate, solvate, polymorph, enantiomer, diastereomer and mixtures thereof.

It was found that the compounds of the present invention show superior pharmaceutical and/or pharmacokinetic properties. In particular, the compounds show an advantageous hydrolyzation rate so that the lower dose of the compound can be applied to the patient.

Another subject of the invention is a compound according to Formula (I), (II) or (IIa) with the proviso that the compound is not represented by Formula (III), or a compound according to Formula (VIII) for use as a medicament.

Further, the present invention relates to a compound according to Formula (I), (II) or (IIa) with the proviso that the compound is not represented by Formula (III), or a compound according to Formula (VIII) for use in the treatment of systemic diseases, autoimmune diseases of inflammatory diseases like rheumatoid arthritis, preferably for use in the treatment of multiple sclerosis or psoriasis, in particular multiple sclerosis.

Another subject is a pharmaceutical composition comprising the above-mentioned compound according to Formula (I), (II) or (IIa) with the proviso that the compound is not represented by Formula (III), or a compound according to Formula (VIII).

DETAILED DESCRIPTION OF THE INVENTION

Figure 1:
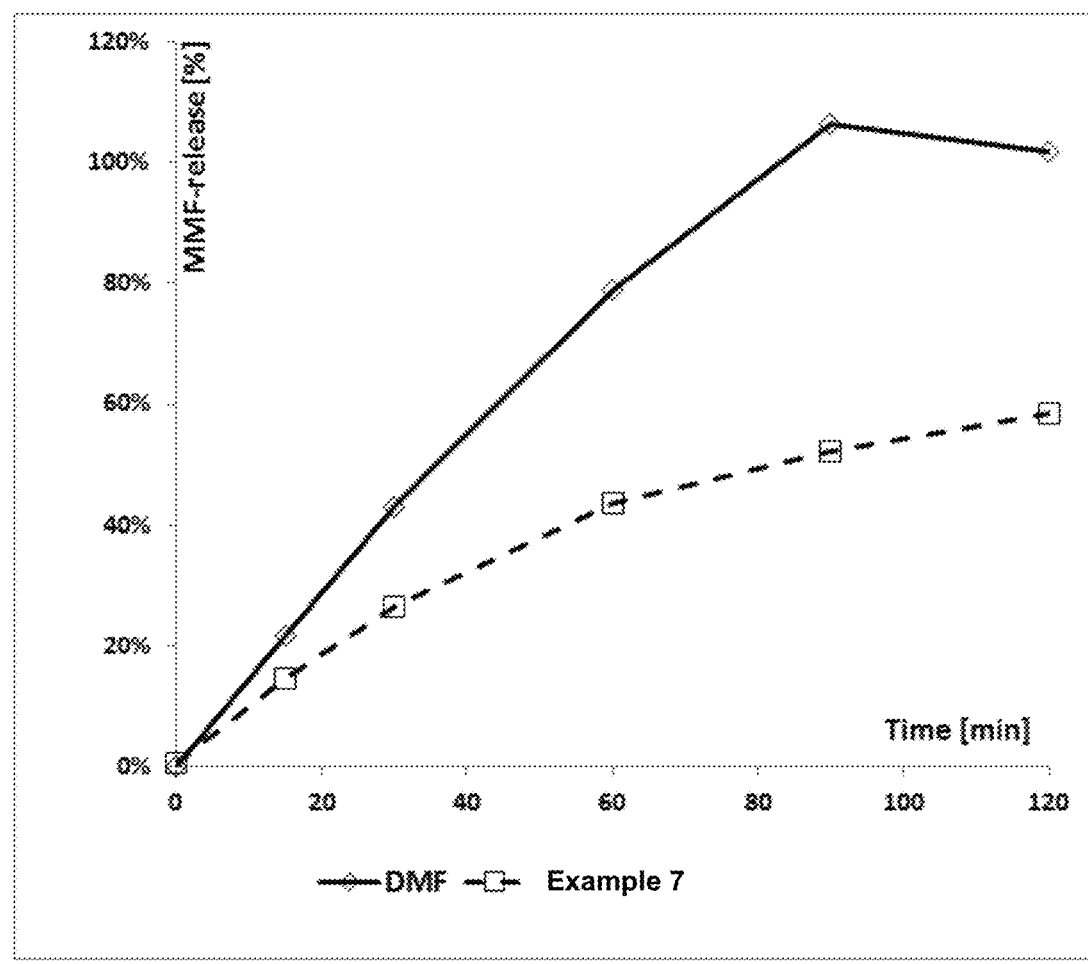
FIG. 1 shows that compounds according to Formula (II) have a significantly slower hydrolyzation to MMF than DMF.

In the context of this invention, the compound of the present invention is represented by the above Formula (I), (II) or (IIa) or by the above Formula (VIII). Further, the compound may refer to pharmaceutically acceptable salts, hydrates, solvates, polymorphs, stereoisomers like enantiomers or diastereomers and mixtures thereof. For example, the invention also refers to enantiomers of pharmaceutically acceptable salts of compounds according to Formula (I) or (II), (IIa) or Formula (VIII) or to solvates of salts or hydrates or polymorphs or the like. The same applies to all embodiments, e.g. to compounds of Formulae (VI), (V), (VI) and (VII) or compounds of Formulae (IX), (X), (XI), (XII), (XIII), (XIV), (XV) and (XVI).

In a particularly preferred embodiment of the present invention a single compound according to Formula (I), (II) or (IIa) or to Formula (VIII) can be used as a medicament.

The same applies to the pharmaceutical composition comprising the compound(s) represented by Formula (I), (II) or (IIa) or by Formula (VIII).

In a preferred embodiment of the invention in a compound according Formula (I) $R^3$ is —COR$^{31}$ or —(CH$_2$)$_n$—OH with n being 1, 2 or 3, wherein $R^{31}$ is —OR$^{32}$ or $NR^{33}R^{34}$ with $R^{32}$, $R^{33}$ and $R^{34}$ being independently hydrogen or alkyl with 1 to 4 carbon atoms.

In an alternative preferred embodiment $R^{31}$ can preferably be hydrogen.

A compound according to Formula (I) with $R^3$ being $COR^{31}$, wherein $R^{31}$ is $-OR^{32}$ or $NR^{33}R^{34}$ with $R^{32}$, $R^{33}$ and $R^{34}$ being independently hydrogen or alkyl with 1 to 4 carbon atoms can be regarded as a 2,3-dihydroxy propionic acid (amide) wherein one or both hydroxyl groups are esterified with MMF.

Alternatively, compound according to Formula (I) with $R^3$ being COH can be regarded as a 2,3-dihydroxy propionic aldehyde wherein one or both hydroxyl groups are esterified with MMF.

Alkyl with 1 to 4 carbon atoms can for example include methyl, ethyl, propyl, isopropyl, butyl, isobutyl, and tert-.butyl.

In a more preferred embodiment of the invention in a compound according Formula (I) $R^3$ is $-(CH_2)_n-OH$ with n being 1, 2 or 3.

A compound according to Formula (I) with $R^3$ being $-(CH_2)_n-OH$ with n being 1, 2 or 3 can be regarded as propane-1,2,3-triol (glycerol), butane-1,2,4-triol or pentane-1,2,5-triol wherein one or both 1,2-hydroxy groups are esterified with MMF.

In a particularly preferred embodiment of the invention in a compound according Formula (I)
$R^1$ is trans $-CO-CH=CH-COOCH_3$,
$R^2$ is hydrogen, and
$R^3$ is $-(CH_2)_n-OH$ with n being 1.

In an alternative particularly preferred embodiment of the invention in a compound according Formula (I)
$R^1$ is hydrogen,
$R^2$ is trans $-CO-CH=CH-COOCH_3$, and
$R^3$ is $-(CH_2)_n-OH$ with n being 1.

Thus, in an especially preferred embodiment the compound according to Formula (I) is selected from the compounds according to Formulae (IV) and (V)

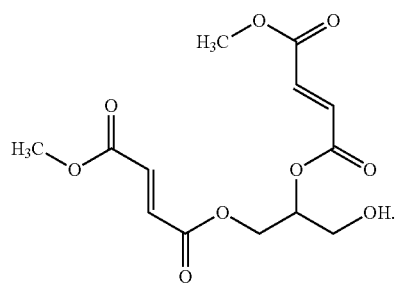

Formula (IV)

and

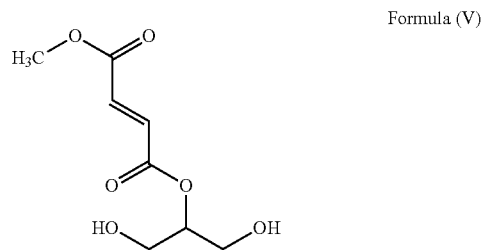

Formula (V)

In a preferred embodiment of the invention in a compound according Formula (I)
$R^1$ and $R^2$ are trans $-CO-CH=CH-COOCH_3$, and
$R^3$ is $-COR^{31}$ or $-(CH_2)_n-OH$ with n being 1, 2 or 3, wherein
$R^{31}$ is $-OR^{32}$ or $NR^{33}R^{34}$ with $R^{32}$, $R^{33}$ and $R^{34}$ being independently hydrogen or alkyl with 1 to 4 carbon atoms.
$R^3$, $R^{31}$, $R^{32}$, $R^{33}$, $R^{34}$, n and alkyl corresponds to the definitions mentioned above.

In an alternative more preferred embodiment in a compound according Formula (I) $R^1$ and $R^2$ are trans $-CO-CH=CH-COOCH_3$, and
$R^3$ is $-(CH_2)_n-OH$ with n being 1.

Thus, in an especially preferred embodiment the compound according to Formula (I) is the compound according to Formula (VI)

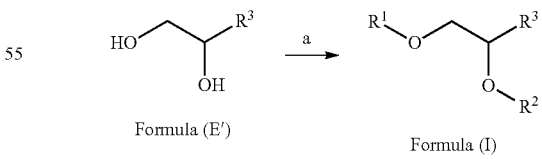

Formula (VI)

In a preferred embodiment a compound according to Formula (I) comprises a stereocenter.

In a preferred embodiment the compound according to Formula (I) is present as racemate.

In an alternative preferred embodiment the compound according to Formula (I) is present as (R)-enantiomer.

In a further alternative preferred embodiment the compound according to Formula (I) is present as (S)-enantiomer.

In a preferred embodiment a compound according to Formula (IV) comprises a stereocenter.

In a preferred embodiment the compound according to Formula (IV) is present as racemate.

In an alternative preferred embodiment the compound according to Formula (IV) is present as (R)-enantiomer.

In a further alternative preferred embodiment the compound according to Formula (IV) is present as (S)-enantiomer.

In a preferred embodiment a compound according to Formula (VI) comprises a stereocenter.

In a preferred embodiment the compound according to Formula (VI) is present as racemate.

In an alternative preferred embodiment the compound according to Formula (VI) is present as (R)-enantiomer.

In a further alternative preferred embodiment the compound according to Formula (VI) is present as (S)-enantiomer.

A compound according to Formula (I) can preferably be synthesized via the following route:

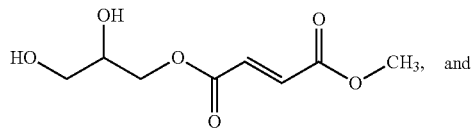

Formula (E')     Formula (I)

Preferably, in step a compound according to Formula (E') and a MMF can be submitted to an esterification in an organic solvent in the presence of a coupling agent. A coupling agent is preferably a substance generally facilitating the formation of an ester or an amide. The coupling agent reacts with a carboxy group by forming a reactive intermediate which is subsequently further reacted with an alcohol or an amine to form the final product, i.e. an ester or an amide. Suitable coupling agents can be for example DCC (N,N'-dicyclohexylcarbodiimide), DIC (N,N'-diisopropylcarbodiimide), EDC (N-ethyl-N'-(3-methylaminopropyl) carbo-diimide hydrochloride), CDI (carbonyldiimidazole), preferably EDC. It is further preferred that the coupling reaction is carried in the presence of an auxiliary alkaline compound. Suitable alkaline compounds are for example pyridine and amines, such as triethylamine, and diisopropylethylamine and DMAP (4-(dimethylamino)pyridine), in particular DMAP.

A suitable organic solvent can for example be dichloromethane, chloroform, acetonitrile, dioxane, tetrahydrofuran and dimethylformamide.

Alternatively, MMF can be preferably reacted with thionyl chloride or oxalyl chloride, preferably oxalyl chloride, to form the corresponding acid chloride.

Subsequently, the corresponding acid chloride can be submitted to a reaction with the compound according to Formula (E'), preferably in an organic solvent such as dioxane, tetrahydrofuran, chloroform or dichloromethane. Further, the reaction of the acid chloride with compound according the compound according to Formula (E') is preferably carried out in the presence of an auxiliary alkaline compound.

Suitable alkaline compounds are for example pyridine and amines, such as triethylamine, and diisopropylethylamine, preferably triethylamine.

Alternatively, the above acid chloride of MMF can be further transferred in activated esters like the para-nitrophenol ester.

Further alternatively, MMF can be reacted with acid chlorides, diphenylphosphoryl azide or chlorosulfonyl isocyanate to form (mixed) anhydrides. These mixed anhydrides can be also submitted to further reactions to obtain to further forms of anhydrides. For example, the anhydride of monomethylfumarate can be obtained by said preparation.

Subsequently, an activated ester or MMF anhydride can be submitted to a reaction with the compound according to Formula (E'), preferably in an organic solvent such as dioxane, tetrahydrofuran, chloroform, acetone or dichloromethane. Further, the reaction of an activated ester or MMF anhydride with a compound according to Formula (E') is preferably carried out in the presence of an auxiliary alkaline compound. Suitable alkaline compounds are for example pyridine and amines, such as triethylamine, diisopropylethylamine and DMAP (4-(dimethylamino)pyridine), preferably DMAP.

Alternatively, the reaction of the activated ester or MMF anhydride with compound according the compound according to Formula (E') can preferably be carried out the absence of an auxiliary alkaline compound.

A suitable organic solvent can for example be dioxane, tetrahydrofuran and dimethylformamide.

In a preferred embodiment one or two of the hydroxyl groups of the compound according to Formula (E') can be protected with a protection group before being submitted to a reaction with MMF in presence of a coupling agent or with the acid chloride of MMF. Such a protection group can for example be trialkylsilyl group.

Alternatively, two hydroxy groups might be reacted with a ketone, such as acetone, to form an acetal group as a protection group.

After the coupling reaction the protection group can preferably be removed by a suitable reaction.

In an alternative embodiment in a compound according to Formula (II)
$R^4$ is hydrogen or trans —CO—CH=CH—COOCH$_3$ and
$R^5$ is —(CH$_2$)$_n$COR$^{51}$ or —(CH$_2$)$_n$—OH with n being 0, 1 or 2, wherein
$R^{51}$ is —OR$^{52}$ or NR$^{53}$R$^{54}$ with $R^{52}$, $R^{53}$ and $R^{54}$ being independently hydrogen or alkyl with 1 to 4 carbon atoms.

In a preferred embodiment $R^4$ is trans —CO—CH=CH—COOCH$_3$.

$R^5$, $R^{51}$, $R^{52}$, $R^{53}$, $R^{54}$, n and alkyl corresponds to the definitions as given above with reference to the terms of Formula (I).

In a further preferred embodiment in a compound according to Formula (II)
$R^4$ is trans —CO—CH=CH—COOCH$_3$ and
$R^5$ is —(CH$_2$)$_n$—OH with n being 0, 1 or 2, in particular with n being 0.

In an especially preferred embodiment the compound according to Formula (II) is the compound according to of Formula (VII)

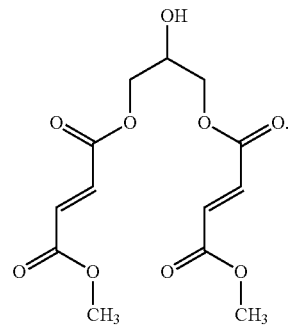

Formula (VII)

In a preferred embodiment a compound according to Formula (II) comprises a stereocenter.

In a preferred embodiment the compound according to Formula (II) is present as racemate.

In an alternative preferred embodiment the compound according to Formula (II) is present as (R)-enantiomer.

In a further alternative preferred embodiment the compound according to Formula (II) is present as (S)-enantiomer.

A compound according to Formula (II) can preferably be synthesized via the following route:

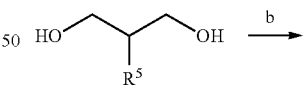

Formula (E″)

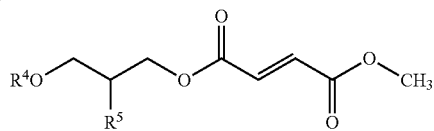

Formula (II)

Preferably, in step b a compound according to Formula (E″) and MMF can be submitted to an esterification in an organic solvent in the presence of a coupling agent. A coupling agent is preferably a substance generally facilitating the formation of an ester or an amide. The coupling agent reacts with a carboxy group by forming a reactive intermediate which is subsequently further reacted with an alcohol or an amine to form the final product, i.e. an ester or an amide. Suitable coupling agents can be for example DCC (N,N'-dicyclohexylcarbodiimide), DIC (N,N'-diisopropylcarbodiimide), EDC (N-ethyl-N'-(3-methylaminopropyl) carbo-diimide hydrochloride), CDI (carbonyldiimidazole), preferably EDC. It is further preferred that the coupling reaction is carried in the presence of an auxiliary alkaline compound. Suitable alkaline compounds are for example pyridine and amines, such as triethylamine, and diisopropylethylamine and DMAP (4-(dimethylamino)pyridine), in particular DMAP.

A suitable organic solvent can for example be dichloromethane, chloroform, acetonitrile, dioxane, tetrahydrofuran and dimethylformamide.

Alternatively, MMF can be preferably reacted with thionyl chloride or oxalyl chloride, preferably oxalyl chloride, to form the corresponding acid chloride. Subsequently, the corresponding acid chloride can be submitted to a reaction with the compound according to Formula (E''), preferably in an organic solvent such as dioxane, tetrahydrofuran, chloroform or dichloromethane. Further, the reaction of the acid chloride with compound according the compound according to Formula (E'') is preferably carried in the presence of an auxiliary alkaline compound. Suitable alkaline compounds are for example pyridine and amines, such as triethylamine, and diisopropylethylamine, preferably triethylamine.

Alternatively, the above acid chloride of MMF can be further transferred in activated esters like the para-nitrophenol ester.

Further alternatively, MMF can be reacted with acid chlorides, diphenylphosphoryl azide or chlorosulfonyl isocyanate to form (mixed) anhydrides. These mixed anhydrides can be also submitted to further reactions to obtain to further forms of anhydrides. For example, the anhydride of monomethylfumarate can be obtained by said preparation.

Subsequently, an activated ester or MMF anhydride can be submitted to a reaction with the compound according to Formula (E''), preferably in an organic solvent such as dioxane, tetrahydrofuran, chloroform, acetone or dichloromethane. Further, the reaction of an activated ester or MMF anhydride with a compound according the compound according to Formula (E'') is preferably carried out in the presence of an auxiliary alkaline compound. Suitable alkaline compounds are for example pyridine and amines, such as triethylamine, diisopropylethylamine and DMAP (4-(dimethylamino)pyridine), preferably DMAP.

Alternatively, the reaction of the activated ester or MMF anhydride with compound according the compound according to Formula (E'') can preferably be carried out the absence of an auxiliary alkaline compound.

A suitable organic solvent can for example be dioxane, tetrahydrofuran and dimethylformamide.

In a preferred embodiment one or two of the hydroxyl groups of the compound according to Formula (E'') can be protected with a protection group before being submitted to a reaction with MMF in presence of a coupling agent or with the acid chloride of MMF. Such a protection group can for example be trialkylsilyl group. Alternatively, two hydroxy groups might be reacted with a ketone, such as acetone, to form an acetal group as a protection group.

After the coupling reaction the protection group can be preferably removed by a suitable reaction.

In a preferred embodiment residues in a compound according to Formula (I) are chosen such that they do not correspond to a compound according to Formula (II).

A compound according to Formula (IIa) can preferably be synthesized via the following route:

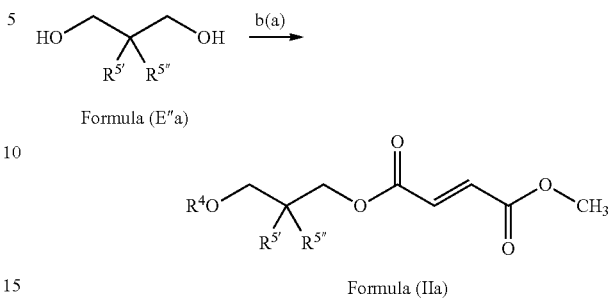

Formula (E''a)

Formula (IIa)

Preferably, in step b(a) a compound according to Formula (E''a) and MMF can be submitted to an esterification in an organic solvent in the presence of a coupling agent. A coupling agent is preferably a substance generally facilitating the formation of an ester or an amide. The coupling agent reacts with a carboxy group by forming a reactive intermediate which is subsequently further reacted with an alcohol or an amine to form the final product, i.e. an ester or an amide. Suitable coupling agents can be for example DCC (N,N'-dicyclohexylcarbodiimide), DIC (N,N'-diisopropylcarbodiimide), EDC (N-ethyl-N'-(3-methylaminopropyl) carbo-diimide hydrochloride), CDI (carbonyldiimidazole), preferably EDC. It is further preferred that the coupling reaction is carried out in the presence of an auxiliary alkaline compound. Suitable alkaline compounds are for example pyridine and amines, such as triethylamine, and diisopropylethylamine and DMAP (4-(dimethylamino)pyridine), in particular DMAP.

A suitable organic solvent can for example be dichloromethane, chloroform, acetonitrile, dioxane, tetrahydrofuran and dimethylformamide.

Alternatively, MMF can be preferably reacted with thionyl chloride or oxalyl chloride, preferably oxalyl chloride, to form the corresponding acid chloride. Subsequently, the corresponding acid chloride can be submitted to a reaction with the compound according to Formula (E''a), preferably in an organic solvent such as dioxane, tetrahydrofuran, chloroform or dichloromethane. Further, the reaction of the acid chloride with the compound according to Formula (E''a) is preferably carried out in the presence of an auxiliary alkaline compound. Suitable alkaline compounds are for example pyridine and amines, such as triethylamine, and diisopropylethylamine, preferably triethylamine.

Alternatively, the above acid chloride of MMF can be further transferred in activated esters like the para-nitrophenol ester.

Further alternatively, MMF can be reacted with acid chlorides, diphenylphosphoryl azide or chlorosulfonyl isocyanate to form (mixed) anhydrides. These mixed anhydrides can be also submitted to further reactions to obtain further forms of anhydrides. For example, the anhydride of monomethylfumarate can be obtained by said preparation.

Subsequently, an activated ester or MMF anhydride can be submitted to a reaction with the compound according to Formula (E''a), preferably in an organic solvent such as dioxane, tetrahydrofuran, chloroform, acetone or dichloromethane. Further, the reaction of an activated ester or MMF anhydride with the compound according to Formula (E''a) is preferably carried out in the presence of an auxiliary alkaline compound. Suitable alkaline compounds are for example pyridine and amines, such as triethylamine, diisopropylethylamine and DMAP (4-(dimethylamino)pyridine), preferably DMAP.

Alternatively, the reaction of the activated ester or MMF anhydride with the compound according to Formula (E"a) can preferably be carried out in the absence of an auxiliary alkaline compound.

A suitable organic solvent can for example be dioxane, tetrahydrofuran and dimethylformamide.

In a preferred embodiment one or two of the hydroxyl groups of the compound according to Formula (E"a) can be protected with a protection group before being submitted to a reaction with MMF in presence of a coupling agent or with the acid chloride of MMF. Such a protection group can for example be a trialkylsilyl group. Alternatively, two hydroxy groups might be reacted with a ketone, such as acetone, to form an acetal group as a protection group.

After the coupling reaction the protection group can preferably be removed by a suitable reaction.

In a preferred embodiment of the invention in a compound according Formula (VIII) $R^6$ can be —CO—$CH_2$CH(OH)$CH_2N^{\oplus}(CH_3)_3X^{\ominus}$.

$X^{\ominus}$ is a pharmaceutically acceptable anion. Examples of said anion are oxide, hydroxide, halogenides such as fluoride, chloride, bromide or iodide, nitrate, carbonate, hydrogen carbonate, sulphate, hydrogen sulphate, phosphate, monohydrogen phosphate, dihydrogen phosphate, nitrate and residues derived from organic acids, such as acetate, succinate, propionate, tartrate, oxalate, maleate, citrate, benzoate or lactate.

Further, $R^7$ can preferably be hydrogen.

Alternatively preferred $R^7$ can be trans-CO—CH=CH—COOCH$_3$.

Thus, in an especially preferred embodiment the compound according to Formula (VIII) is selected from the compounds according to Formulae (IX) and (X):

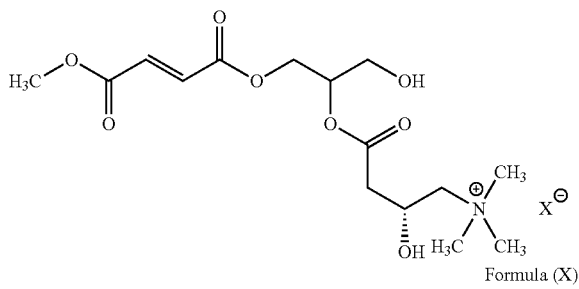

Formula (IX)

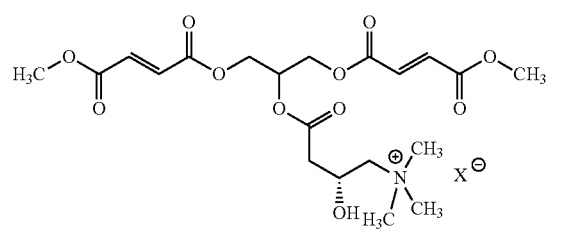

Formula (X)

In an alternatively preferred embodiment of the invention in a compound according Formula (VIII) $R^6$ can be —CO—$CH_2$CH(OCOCH$_3$)$CH_2N^{\oplus}(CH_3)_3X^{\ominus}$.

Further, $R^7$ can preferably be hydrogen.

Alternatively preferred $R^7$ can be trans-CO—CH=CH—COOCH$_3$.

Thus, in an especially preferred embodiment the compound according to Formula (VIII) is selected from the compounds according to Formulae (XI) and (XII):

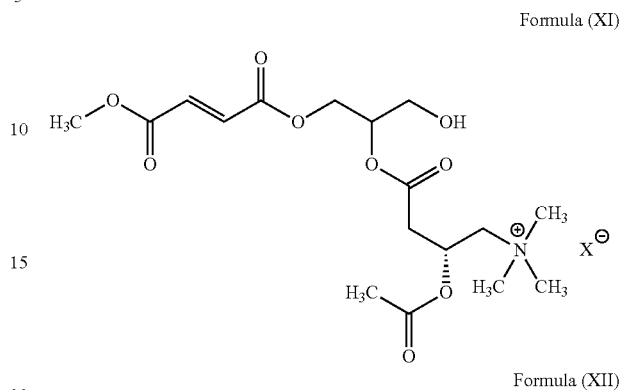

Formula (XI)

Formula (XII)

In a preferred embodiment of the invention in a compound according Formula (VIII) $R^7$ can be —CO—$CH_2$CH(OH)$CH_2N^{\oplus}(CH_3)_3X^{\ominus}$.

Further, $R^6$ can preferably be hydrogen.

Alternatively preferred $R^6$ can be trans-CO—CH=CH—COOCH$_3$.

Thus, in an especially preferred embodiment the compound according to Formula (VIII) is selected from the compounds according to Formulae (XIII) and (XIV):

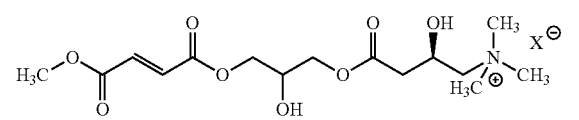

Formula (XIII)

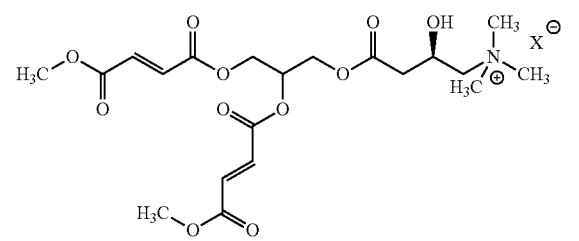

Formula (XIV)

In an alternatively preferred embodiment of the invention in a compound according to Formula (VIII) $R^7$ can be —CO—$CH_2$CH(OCOCH$_3$)$CH_2N^{\oplus}(CH_3)_3X^{\ominus}$.

Further, $R^6$ can preferably be hydrogen.

Alternatively preferred $R^6$ can be trans-CO—CH=CH—COOCH$_3$.

Thus, in an especially preferred embodiment the compound according to Formula (VIII) is selected from the compounds according to Formulae (XV) and (XVI):

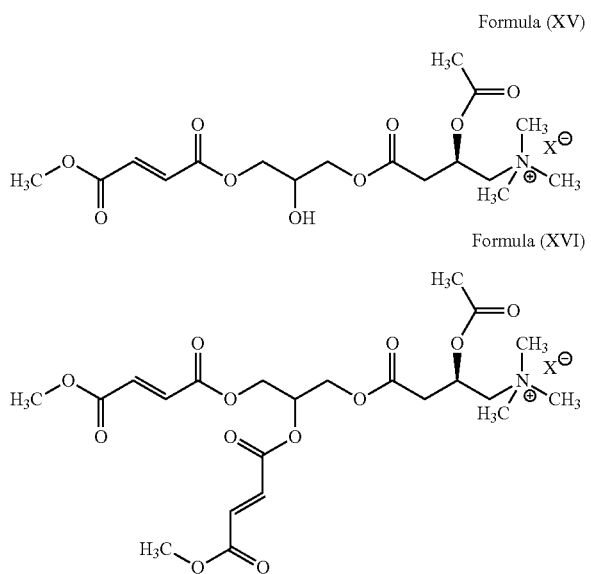

In a preferred embodiment a compound according to Formula (VIII) comprises two stereocenters.

In a preferred embodiment the compound according to Formula (VIII) is present as a diastereomer.

In an alternatively preferred embodiment the compound according to Formula (VIII) is present as an enantiomer.

A compound according to Formula (VIII) can preferably be synthesized via the following route:

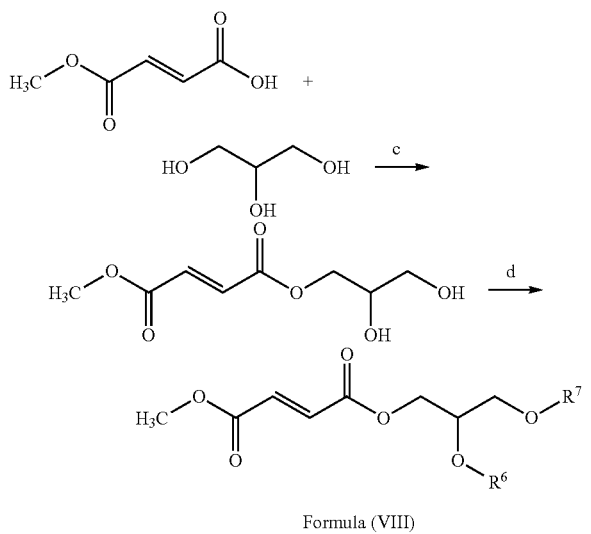

Preferably, in step c, MMF and glycerol can be submitted to an esterification in an organic solvent in the presence of a coupling agent.

Generally the reaction condition of step c can correspond to the ones as described above with regard to step a.

A coupling agent is preferably a substance generally facilitating the formation of an ester or an amide. The coupling agent reacts with a carboxy group by forming a reactive intermediate which is subsequently further reacted with an alcohol or an amine to form the final product, i.e. an ester or an amide. Suitable coupling agents can be for example DCC (N,N'-dicyclohexylcarbodiimide), DIC (N,N'-diisopropylcarbodiimide), EDC (N-ethyl-N'-(3-methylaminopropyl)carbodiimide hydrochloride), CDI (carbonyldiimidazole), preferably EDC. It is further preferred that the coupling reaction is carried out in the presence of an auxiliary alkaline compound. Suitable alkaline compounds are for example pyridine and amines, such as triethylamine, and diisopropylethylamine and DMAP (4-(dimethyl-amino)pyridine), in particular DMAP.

A suitable organic solvent can for example be dichloromethane, chloroform, acetonitrile, dioxane, tetrahydrofuran and dimethylformamide.

Alternatively, MMF can be preferably reacted with thionyl chloride or oxalyl chloride, preferably oxalyl chloride, to form the corresponding acid chloride. Subsequently, the corresponding acid chloride can be submitted to a reaction with glycerol, preferably in an organic solvent such as dioxane, tetrahydrofuran, chloroform or dichloromethane. Further, the reaction of the acid chloride with glycerol is preferably carried out in the presence of an auxiliary alkaline compound. Suitable alkaline compounds are for example pyridine and amines, such as triethylamine, and diisopropylethylamine, preferably triethylamine.

Alternatively, the above acid chloride of MMF can be further transferred in activated esters like the para-nitrophenol ester.

Further alternatively, MMF can be reacted with acid chlorides, diphenylphosphoryl azide or chlorosulfonyl isocyanate to form (mixed) anhydrides. These (mixed) anhydrides can be also submitted to further reactions to obtain further forms of anhydrides. For example, the anhydride of monomethylfumarate can be obtained by said preparation.

Subsequently, an activated ester or MMF anhydride can be submitted to a reaction with glycerol, preferably in an organic solvent such as dioxane, tetrahydrofuran, chloroform, acetone or dichloromethane. Further, the reaction of an activated ester or MMF anhydride with glycerol is preferably carried out in the presence of an auxiliary alkaline compound. Suitable alkaline compounds are for example pyridine and amines, such as triethylamine, diisopropylethylamine and DMAP (4-(dimethylamino)pyridine), preferably DMAP.

Alternatively, the reaction of the activated ester or MMF anhydride with glycerol can preferably be carried out the absence of an auxiliary alkaline compound.

A suitable organic solvent can for example be dioxane, tetrahydrofuran and dimethylformamide.

In a preferred embodiment one or two of the hydroxyl groups of glycerol can be protected with a protection group before being submitted to a reaction with MMF in the presence of a coupling agent or with the acid chloride of MMF. Such a protection group can for example be a trialkylsilyl group. Alternatively and more preferably, two hydroxy groups might be reacted with a ketone, such as acetone, to form an acetal group as a protection group.

After the coupling reaction the protection group can preferably be removed by a suitable reaction.

Preferably, in step d the product from step c acetyl carnitine can be submitted to an esterification in an organic solvent in the presence of a coupling agent. Generally the reaction condition of step d can correspond to the ones as described above with regard to step c.

Alternatively conversion can be performed via enzyme reaction.

In a further preferred embodiment the hydroxy group of carnitine can preferably be protected with a protection group before being submitted to the esterification with the product from step c in reaction step d. Such a protection group can for example be a trialkylsilyl group. After the coupling reaction the protection group can preferably be removed by a suitable reaction.

In an alternatively preferred embodiment, the product from step d and further MMF can be submitted in a reaction step d' to an esterification in an organic solvent in the presence of a coupling agent. Generally the reaction condition of step d' can correspond to the ones described above with regard to step c. The product from step d' can be regarded as a glycerol wherein one of the three hydroxy groups is esterified with a carnitine or acetyl carnitine and two of the three hydroxy groups are esterified with MMF.

In the present application carnitine refers to (R)-carnitine as well as to (S)-carnitine, preferably to (R)-carnitine.

In the present application acetyl carnitine refers to (R)-acetyl carnitine as well as (S)-acetyl carnitine, preferably (R)-acetyl carnitine.

The above compounds according to Formula (I), (II) and (IIa) and to Formula (VIII) show excellent pharmacokinetic properties. Within two hours the compounds show a hydrolyzation into MMF and remaining organic residue wherein the hydrolyzation is significantly slower than the one of DMF. As a result, a smaller amount of MMF is released within the two hours and thus the compounds can be referred to as compounds (prodrugs of MMF) with an intrinsically retarded release of MMF. Additionally, the remaining organic residue is not expected to harm the patient's organism.

Further, the present invention relates to the inventive compounds according to Formula (I), (II) or (IIa) or to Formula (VIII) for use as a medicament.

A further subject of the invention is the inventive compound according to Formula (I), (II) or (IIa) or to Formula (VIII) for use in the treatment and/or prevention of systemic diseases, autoimmune diseases or inflammatory diseases.

Systemic diseases do not just affect single organs. Instead, these diseases are known to affect a number of organs and tissues or even the body as a whole.

People having an autoimmune disease usually suffer from their immune system mistakenly attacking their own cells of their organism and thus incorrectly responding to substances normally present in the body.

An inflammation can be defined as the response of the body to the occurrence of harmful stimuli which can result in pain, heat, redness, swelling and loss of function of the affected organ.

It is possible that some of the above-mentioned diseases cannot be allocated in one single group of the above-mentioned groups, since they show the symptoms of more than one of them.

In a further preferred embodiment, the inventive compound according to Formulae (I), (II) or (IIa) or to Formula (VIII) is for use in the treatment of multiple sclerosis and psoriasis, preferably multiple sclerosis. The compounds of the present invention can e.g. be used in the treatment of the following types of multiple sclerosis: relapsing-remitting, primary-progressive, secondary-progressive, and progressive-relapsing. In a preferred embodiment the compounds of the present invention are used in the treatment of relapsing-remitting multiple sclerosis.

Further, the present invention also provides a pharmaceutical composition comprising the compound according to the present invention, i.e. a pharmaceutical composition comprising a compound according to Formula (I), (II) or (IIa) or a compound according to Formula (VIII) and optionally pharmaceutical excipients.

In a preferred embodiment the pharmaceutical composition comprises
(i) 0.01 to 10 mmol, more preferably 0.05 to 5 mmol, still more preferably 0.25 to 3.5 mmol and particularly preferred 0.5 to 2.5 mmol of a compound according to Formulae (I), (II) or (IIa) or to Formula (VIII);
(ii) pharmaceutical excipient(s).

In a further preferred embodiment the present composition can comprise one or more further excipients, preferably pharmaceutical excipients as described in the European Pharmacopoeia (Ph.Eur.) and/or in the US Pharmacopoeia (USP).

Examples of pharmaceutical excipients are carriers, binders, fillers, disintegrants, wicking agents, glidants and/or lubricants.

In a preferred embodiment the excipients are chosen such that the resulting formulation is a gastric juice-resistant formulation. In a preferred embodiment the formulation of the present invention does not show significant drug release under acidic conditions. In particular, the in-vitro drug release after 2 hours is less than 10%, preferably 0 to 9.9%, more preferably 0 to 5%, still more preferably 0.001 to 3%, measured according to USP, Apparatus II, paddle, 0.1N HCl, 37° C., 50 rpm.

The pharmaceutical composition can be in a form suitable for oral administration, preferably in the form of a tablet or capsule, in particular in form of a tablet.

It is further preferred that the tablet is coated with a film coating. Alternatively, the capsule could also be coated.

In the present invention, the following three types of film coatings are possible:
film coating without affecting the release of the active ingredient,
gastric juice-resistant film coatings,
retard film coatings.

Generally, film coatings can be prepared by using film-forming agents such as waxes, cellulose derivatives, poly (meth)acrylate, polyvinylpyrrolidone, polyvinyl acetate phthalate, and/or shellac or natural rubbers such as carrageenan.

It is preferred that the present tablet is coated with a gastric juice-resistant film coating. Alternatively, a capsule comprising a gastric juice-resistant film coating can be used.

The gastric juice-resistant film coating preferably is a film coating being stable in the pH range of about 0.7 to 3.0, which is supposed to be the pH-value of human gastric juice found in the stomach. However, in an environment with a pH value of 5 to 9, which is supposed to be present in the (small) intestine of the human body, the gastric juice-resistant film coating preferably dissolves and the drug can be released.

The gastric juice-resistant film coating (often also referred to as enteric coating) can comprise film-forming agents being for example fats, fatty acids, waxes, alginates, shellac, polyvinyl acetate phthalate, cellulose derivatives such as carboxy methyl ethyl cellulose, cellulose acetate succinate, cellulose acetate phthalate, hydroxypropyl methyl cellulose phthalate, hydroxypropyl methyl cellulose acetate succinate, cellulose acetate trimellitate, and meth(acrylic)acid copolymers such as methyl acrylate-methacrylic acid copolymers, methyl methacrylate-methacrylic acid copolymers, Eudragits (for example Eudragit®L30D, Eudragit® L, Eudragit® S).

The coating is preferably free of active ingredient. It is further preferred that the thickness of the coating is usually 10 μm to 2 mm, preferably from 50 to 500 μm.

The preferred coating may comprise a film-forming agent and one or more of the following: lubricant, surfactant, glidant, pigment and water.

The preferred coating according to an embodiment of the present invention can comprise, along with the film-forming agent, e.g. stearic acid as lubricant for plasticizing and dissolving the polymer, sodium lauryl sulfate as a surfactant for wetting and dispersing, talc as glidant, iron oxide yellow and/or titanium oxide as pigment(s) and optionally purified water.

In a preferred embodiment the pharmaceutical composition can be administered one to three times a day, preferably once or twice a day, more preferably once a day.

Further, the present invention relates to a method for treating and/or preventing systemic diseases, autoimmune diseases and/or inflammatory diseases, preferably multiple sclerosis or psoriasis, in particular multiple sclerosis, comprising administering to a subject in need thereof a therapeutically effective amount of the compound of the invention or the pharmaceutical composition of the invention. For the compound and the pharmaceutical composition the same applies as to the compound and the pharmaceutical composition as described above in the text, respectively.

The invention is illustrated by the following examples.

EXAMPLES

Example 1

Synthesis of rac-(E)-But-2-enedioic acid 2,3-dihydroxy-propyl ester methyl ester

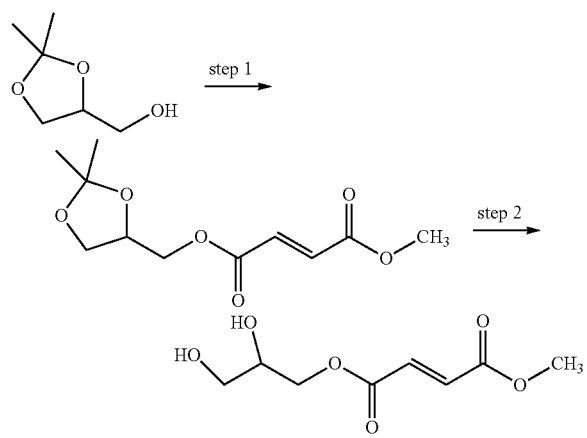

Step 1: rac-(E)-But-2-enedioic acid 2,2-dimethyl-[1,3]dioxolan-4-ylmethyl ester methyl ester Monomethylfumarate (1.65 g; 12.7 mmol), rac-(2,2-Dimethyl-[1,3]dioxolan-4-yl)-methanol (1 g; 8 mmol), N-ethyl-N'-(3-methylaminopropyl)carbodiimide hydrochloride (1.62 g, 8.5 mmol) and 4-(dimethylamino)pyridine (0.05 g, 0.4 mmol) were dissolved in dry dichloromethane (22 ml). The reaction mixture was kept under continuous stirring at room temperature under nitrogen for 5 h. The organic layer was washed with water (20 ml), the aqueous layer was washed with dichloromethane (3×50 ml) and the combined organic layers were dried over anhydrous sodium sulfate, filtered, and concentrated in vacuo. The black oily product was subjected to column chromatography (flash chromatography; eluent: ethylacetate/n-heptane 1/1). The obtained product was subjected once more to column chromatography (eluent: ethylacetate/n-heptane 1/2) to yield the product as colourless oil. After drying the oil on the rotary evaporator at 50° C. for 3 hours, the colourless oil was slowly solidifying to a white solid at room temperature.

Yield: 1.41 g.

$^1$H NMR (400 MHz, CHLOROFORM-d) δ ppm 1.36 (s, 3 H) 1.42 (s, 3 H)3.72-3.78 (m, 1 H)3.80 (s, 3 H) 4.05-4.13 (m, 1 H) 4.17-4.24 (m, 1 H)4.25-4.31 (m, 1 H) 4.32-4.41 (m, 1 H) 6.88 (s, 2 H)

$^{13}$C NMR (100 MHz, CHLOROFORM-d) δ ppm 25.3, 26.7, 52.3, 65.4, 66.2, 73.3, 110.0, 133.1, 133.9, 164.6, 165.2

Step 2: rac-(E)-But-2-enedioic acid 2,3-dihydroxy-propyl ester methyl ester

The acetal resulting from step 1 (6 g; 24.6 mmol) was dissolved in 80% aqueous acetic acid (120 ml) and stirred for 96 hours. The reaction mixture was evaporated to dryness, the resulting oil was crystallizing to a white solid. The solid was suspended in TBME (25 ml) and stirred for 16 hours at room temperature. The precipitate was filtrated off and dried under ambient conditions.

Yield 4.2 g (20.6 mmol)

$^1$H NMR (400 MHz, CHLOROFORM-d) d ppm 2.26-2.96 (m, 2 H) 3.57-3.67 (m, 1 H)3.67-3.77 (m, 1 H) 3.80 (br. s., 3 H) 3.84-3.91 (m, 1 H) 3.93-4.05

$^{13}$C NMR (100 MHz, CHLOROFORM-d) d ppm52.4, 63.2, 66.0, 69.9, 133.0, 134.0, 165.1, 165.3

Example 2

Synthesis of S-(E)-But-2-enedioic acid 2,3-dihydroxy-propyl ester methyl ester

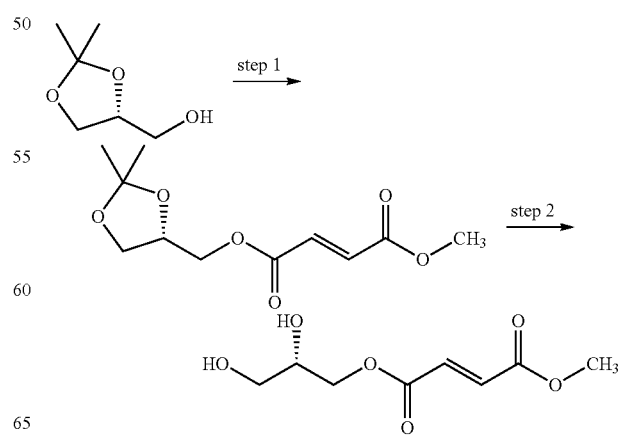

Step 1: S-(E)-But-2-enedioic acid 2,2-dimethyl-[1,3]dioxolan-4-ylmethyl ester methyl ester Monomethylfumarate (1.65 g; 12.7 mmol), R-(2,2-Dimethyl-[1,3]dioxolan-4-yl)-methanol (1 g; 8 mmol), N-ethyl-N'-(3-methylaminopropyl)carbodiimide hydrochloride (1.62 g, 8.5 mmol) and 4-(dimethylamino)pyridine (0.05 g, 0.4 mmol) are dissolved in dry dichloromethane (22 ml). The reaction mixture is kept under continuous stirring at room temperature under nitrogen for 5 h. The organic layer is washed with water (20 ml), the aqueous layer is washed with dichloromethane (3×50 ml) and the combined organic layers are dried over anhydrous sodium sulfate, filtered, and concentrated in vacuo. The black oily product is subjected to column chromatography (flash chromatogry; eluent: ethylacetate/n-heptane 1/1). The obtained product is subjected once more to column chromatography (eluent: ethylacetate/n-heptane 1/2) to yield the product as colourless oil. After drying the oil on the rotary evaporator at 50° C. for 3 hours, the colourless oil is slowly solidifying to a white solid at room temperature.

Step 2: S-(E)-But-2-enedioic acid 2,3-dihydroxy-propyl ester methyl ester Step 2 was carried out as described before in Example 1

Example 3

Synthesis of R-(E)-But-2-enedioic acid 2,3-dihydroxy-propyl ester methyl ester

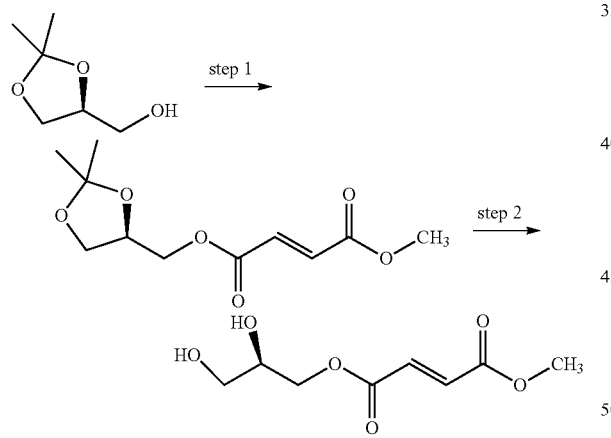

Step 1: R-(E)-But-2-enedioic acid 2,2-dimethyl-[1,3]dioxolan-4-ylmethyl ester methyl ester Monomethylfumarate (1.65 g; 12.7 mmol), S-(2,2-Dimethyl-[1,3]dioxolan-4-yl)-methanol (1 g; 8 mmol), N-ethyl-N'-(3-methylaminopropyl)carbodiimide hydrochloride (1.62 g, 8.5 mmol) and 4-(dimethylamino)pyridine (0.05 g, 0.4 mmol) are dissolved in dry dichloromethane (22 ml). The reaction mixture is kept under continuous stirring at room temperature under nitrogen for 5 h. The organic layer is washed with water (20 ml), the aqueous layer is washed with dichloromethane (3×50 ml) and the combined organic layers are dried over anhydrous sodium sulfate, filtered, and concentrated in vacuo. The black oily product is subjected to column chromatography (flash chromatographie; eluent: EtOAc/n-heptane 1/1). The obtained product is subjected once more to column chromatography (EE/n-heptane 1/2) to yield the product as colourless oil. After drying the oil on the rotary evaporator at 50° C. for 3 hours, the colourless oil is slowly solidifying to a white solid at room temperature.

Step 2: R-(E)-But-2-enedioic acid 2,3-dihydroxy-propyl ester methyl ester (7)

Step 2 was carried out as described before in Example 1.

Example 4

Synthesis of (E)-But-2-enedioic acid 2-hydroxy-1-((E)-3-methoxycarbonyl-acryloyloxymethyl)-ethyl ester methyl ester

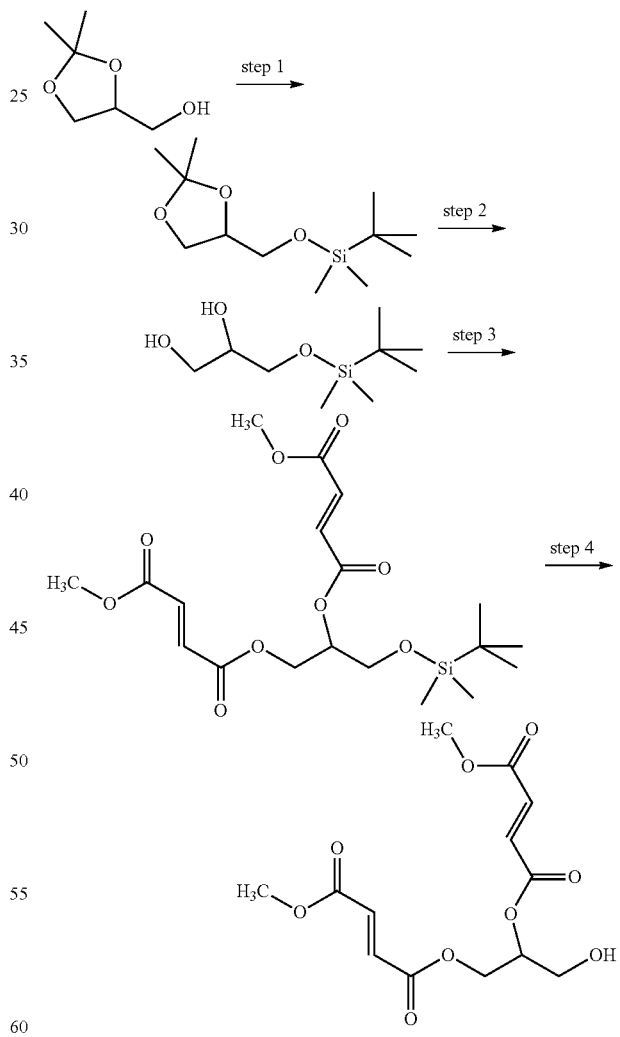

Step 1: tert-Butyldimethyl(2,2-dimethyl-1,3-dioxolan-4-ylmethoxy) silane

Imidazole is added to a flask containing rac-(2,2-Dimethyl-[1,3]dioxolan-4-yl)-methanol in THF. tert-Butyldimethylsilylchloride (TBDMSCl) in THF is added slowly at 0° C. and the resulting mixture stirred at room temperature overnight. The precipitate generated during the reaction is removed by filtration. The filtrate is then diluted in hexane and washed with water. The organic layer is dried over anhydrous MgSO$_4$ and filtered, the solvent is removed by evaporation under reduced pressure to yield the product as an oil.

Step 2:
3-(tert-Butyldimethyl-silanyloxy)-propane-1,2-diol

To a solution of ferric chloride hexahydrate (1.2 g) in acetone (16 mL) is added silica gel (10 g) at room temperature. The solvent is evaporated using rotary evaporator at 30° C. under reduced pressure. The mixture is further kept under vacuum at 60° C. for 30 min. A mixture of 5 mmol of tert-Butyldimethyl(2,2-dimethyl-1,3-dioxolan-4-yl-methoxy) silane and 0.10 g of FeCl$_3$—SiO$_2$ reagent in 20 mL of CHCl$_3$ or CH$_3$COCH$_3$ is stirred at room temperature. The reaction is monitored by GC or TLC. After completion of the reaction, the mixture was filtered, and the filtrate is concentrated under reduced pressure. The product is purified by column chromatography.

Step 3: (E)-But-2-enedioic acid 2-(tert-butyl-dimethyl-silanyloxy)-1-((E)-3-methoxy-carbonyl-acryloyloxymethyl)-ethyl ester methyl ester Monomethylfumarate (0.755 g; 5.8 mmol), rac-3-(tert-Butyldimethyl-silanyloxy)-propane-1,2-diol (1.00 g; 2.3 mmol), N-ethyl-N'-(3-methylaminopropyl)carbodiimide hydrochloride (1.78 g, 9.3 mmol) and 4-(dimethylamino) pyridine (0.01 g, 0.1 mmol) are dissolved in dry dichloromethane (10 ml). The reaction mixture is kept under stirring continuously at room temperature under nitrogen for 5 h. The organic layer is washed with water (20 ml), the aqueous layer is washed with dichloromethane (3×50 ml) and the combined organic layers are dried over anhydrous sodium sulfate, filtered, and concentrated in vacuo. The black oily product is subjected to column chromatography.

Step 4: (E)-But-2-enedioic acid 2-hydroxy-1-((E)-3-methoxycarbonyl-acryloyloxy-methyl)-ethyl ester methyl ester rac-(E)-But-2-enedioic acid 2-(tert-butyl-dimethyl-silanyloxy)-1-((E)-3-methoxy-carbonyl-acryloyloxymethyl)-ethyl ester methyl ester is dissolved in THF and tetrabutylammoniumfluorid is added. The reaction is monitored via TLC. After completion of the reaction, the solvent is evaporated. The obtained crude product is dissolved in ethylacetate and the organic layer is washed with water. After drying of the organic layer over Na$_2$SO$_4$, the solvent is evaporated and the crude product is subjected to flash chromatography to yield the product.

Example 5

Synthesis of R-(E)-But-2-enedioic acid 2-hydroxy-1-((E)-3-methoxy-carbonyl-acryloyloxymethyl)-ethyl ester methyl ester

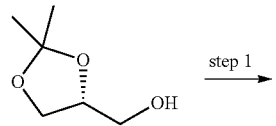

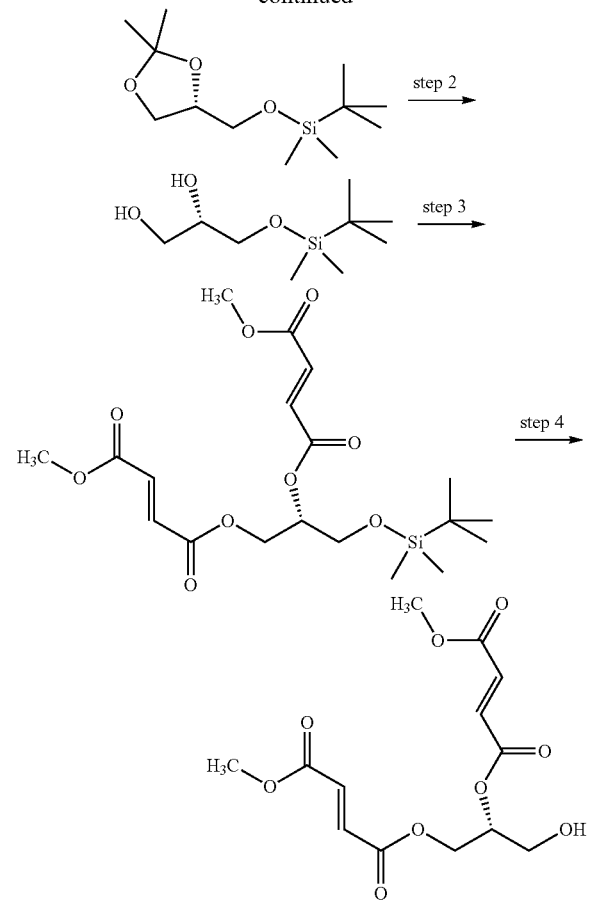

Step 1: S-tert-Butyldimethyl(2,2-dimethyl-1,3-dioxolan-4-ylmethoxy)silane

Imidazole is added to a flask containing R-(2,2-Dimethyl-[1,3]dioxolan-4-yl)-methanol in THF. tert-Butyldimethylsilylchloride (TBDMSCl) in THE is added slowly at 0° C. and the resulting mixture stirred at room temperature overnight. The precipitate generated during the reaction is removed by filtration. The filtrate is then diluted in hexane and washed with water. The organic layer is dried over anhydrous MgSO$_4$ and filtered. The solvent is removed by evaporation under reduced pressure to yield the product as an oil.

Step 2: S-3-(tert-Butyl-dimethyl-silanyloxy)-propane-1,2-diol

To a solution of ferric chloride hexahydrate (1.2 g) in acetone (16 mL) is added silica gel (10 g) at room temperature. The solvent is evaporated using rotary evaporator at 30° C. under reduced pressure. The mixture is further kept under vacuum at 60° C. for 30 min. A mixture of 5 mmol of S-tert-Butyldimethyl(2,2-dimethyl-1,3-dioxolan-4-yl-methoxy) silane and 0.10 g of FeCl$_3$—SiO$_2$ reagent in 20 mL of CHCl$_3$ or CH$_3$COCH$_3$ is stirred at room temperature. The reaction is monitored by GC or TLC. After completion of the reaction, the mixture is filtered, and the filtrate is concentrated under reduced pressure. The product is purified by column chromatography.

Step 3: S-(E)-But-2-enedioic acid 2-(tert-butyl-dimethyl-silanyloxy)-1-((E)-3-methoxy-carbonyl-acryloyloxymethyl)-ethyl ester methyl ester Monomethylfumarate (0.755 g; 5.8 mmol), S-3-(tert-Butyl-dimethyl-silanyloxy)-propane-1,2-diol (1.00 g; 2.3 mmol), N-ethyl-N'-(3-methylaminopropyl)carbodiimide hydrochloride (1.78 g, 9.3 mmol) and 4-(dimethylamino)pyridine (0.01 g, 0.1 mmol) are dissolved in dry dichloromethane (10 ml). The reaction mixture is kept under continuous stirring at room temperature under nitrogen for 5 h. The organic layer is washed with water (20 ml), the aqueous layer is washed with dichloromethane (3×50 ml) and the combined organic layers are dried over anhydrous sodium sulfate, filtered, and concentrated in vacuo. The black oily product is subjected to column chromatography.

Step 4: R-(E)-But-2-enedioic acid 2-hydroxy-1-((E)-3-methoxycarbonyl-acryloyloxy-methyl)-ethyl ester methyl ester S-(E)-But-2-enedioic acid 2-(tert-butyl-dimethyl-silanyloxy)-1-((E)-3-methoxy-carbonyl-acryloyloxymethyl)-ethyl ester methyl ester is dissolved in THF and tetrabutylammoniumfluorid is added. The reaction was monitored via TLC. After completion of the reaction, the solvent is evaporated. The obtained crude product is dissolved in ethylacetate and the organic layer is washed with water. After drying of the organic layer over Na$_2$SO$_4$, the solvent is evaporated and the crude product is subjected to flash chromatography to yield the product.

Example 6

Synthesis of S-(E)-But-2-enedioic acid 2-hydroxy-1-((E)-3-methoxycarbonyl-acryloyloxymethyl)-ethyl ester methyl ester

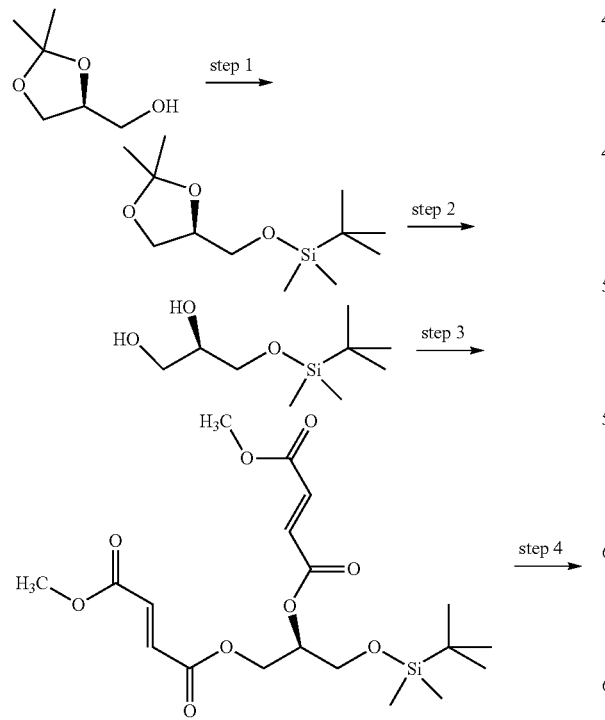

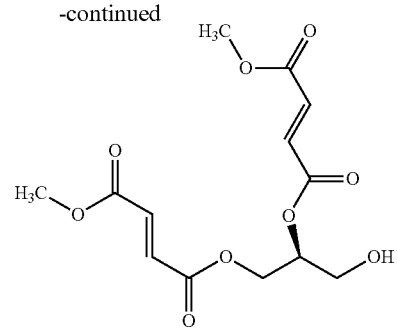

Step 1: R-tert-Butyldimethyl(2,2-dimethyl-1,3-dioxolan-4-ylmethoxy)silane

Imidazole is added to a flask containing S-(2,2-Dimethyl[1,3]dioxolan-4-yl)-methanol in THF. Tert-Butyldimethylsilylchloride (TBDMSCl) in THF is added slowly at 0° C. and the resulting mixture stirred at room temperature overnight. The precipitate generated during the reaction is removed by filtration. The filtrate is then diluted in hexane and washed with water. The organic layer is dried over anhydrous MgSO$_4$ and filtered. The solvent is removed by evaporation under reduced pressure to yield the product as an oil.

Step 2: R-3-(tert-Butyl-dimethyl-silanyloxy)-propane-1,2-diol

To a solution of ferric chloride hexahydrate (1.2 g) in acetone (16 mL) is added silica gel (10 g) at room temperature. The solvent is evaporated using a rotary evaporator at 30° C. under reduced pressure. The mixture is further kept under vacuum at 60° C. for 30 min. silane and 0.10 g of FeC$_3$—Si$_2$ reagent in 20 mL of CHC$_3$ or CH$_3$COCH$_3$ is stirred at room temperature. The reaction is monitored by GC or TLC. After completion of the reaction, the mixture is filtered, and the filtrate was concentrated under reduced pressure. The product is purified by column chromatography.

Step 3: R-(E)-But-2-enedioic acid 2-(tert-butyl-dimethyl-silanyloxy)-1-((E)-3-methoxy-carbonyl-acryloyloxymethyl)-ethyl ester methyl ester Monomethylfumarate (0.755 g; 5.8 mmol), R-3-(tert-Butyl-dimethyl-silanyloxy)-propane-1,2-diol (1.00 g; 2.3 mmol), N-ethyl-N'-(3-methylaminopropyl)carbodiimide hydrochloride (1.78 g, 9.3 mmol) and 4-(dimethylamino)pyridine (0.01 g, 0.1 mmol) are dissolved in dry dichloromethane (10 ml). The reaction mixture is kept under continuous stirring at room temperature under nitrogen for 5 h. The organic layer is washed with water (20 ml), the aqueous layer is washed with dichloromethane (3×50 ml) and the combined organic layers are dried over anhydrous sodium sulfate, filtered, and concentrated in vacuo. The black oily product is subjected to column chromatography.

Step 4: S-(E)-But-2-enedioic acid 2-hydroxy-1-((E)-3-methoxycarbonyl-acryloyloxy-methyl)-ethyl ester methyl ester R-(E)-But-2-enedioic acid 2-(tert-butyl-dimethyl-silanyloxy)-1-((E)-3-methoxy-carbonyl-acryloyloxymethyl)-ethyl ester methyl ester is dissolved in THF and tetrabutylammo-

Example 7

Synthesis of (E)-But-2-enedioic acid 2,3-bis-((E)-methoxycarbonyl-acryloyloxy)-propyl ester methyl ester Route a)

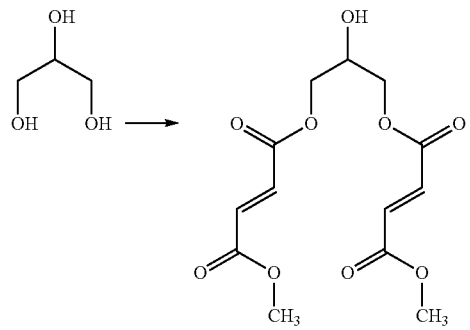 [SMILES: OCC(O)CO ; COC(=O)/C=C/C(=O)OCC(O)COC(=O)/C=C/C(=O)OC]

Propane-1,2,3-triol(Glycerin, 4 g, 18 mmol), monomethylfumarate (4.74 g, 36.6 mmol), N-ethyl-N'-(3-methylaminopropyl)carbodiimide hydrochloride (10.49 g; 54.7 mmol), and 4-(dimethylamino)pyridine (0.11 g, 0.9 mmol) were dissolved in dry dichloromethane (46 ml). The reaction mixture was kept under continuous stirring at room temperature for 16 h. The organic layer was washed with water (40 ml), the aqueous layer was washed with dichloromethane (3×100 ml) and the combined organic layers were dried over anhydrous sodium sulfate, filtered, and concentrated in vacuo. The brownish/orange oily product was subjected to column chromatography (eluent: ethylacetate/n-heptane 1/1), obtaining the product as a colourless solid.

Yield: 474 mg $^1$H NMR (400 MHz, CHLOROFORM-d) δ ppm 2.63-2.88 (br s., 1 H) 3.79 (s., 6 H) 4.14-4.22 (m, 1 H) 4.23-4.37 (m, 4 H) 6.87 (br. s., 4 H)

$^{13}$C NMR (100 MHz, CHLOROFORM-d) δ ppm 52.4, 65.8, 67.8, 132.8, 134.1, 164.7, 165.1

Route b)

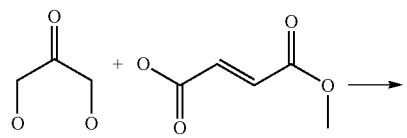

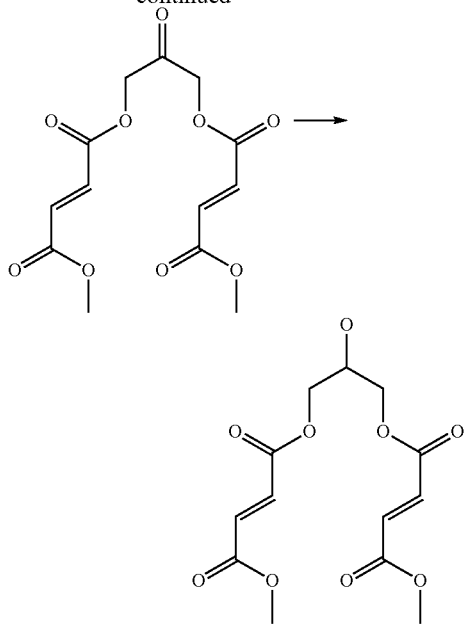

Synthesis of (E)-But-2-enedioic acid 3-((E)-3-methoxycarbonyl-acryloyloxy)-2-oxo-propyl ester methyl ester

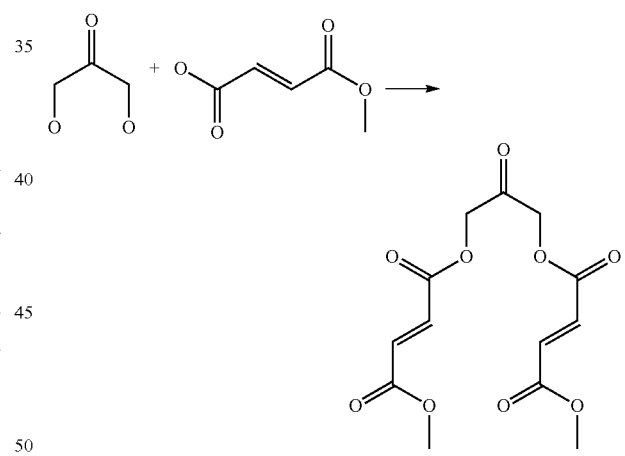

To a solution of dihydroxyacetone (5 g; 55.51 mmol) in THF (150 ml) were added EDCxHCl (22.35 g; 116.6 mmol) and DMAP (0.68 g; 5.6 mmol) at 0° C. A solution of monomethylfumarate (15.16 g (116.6 mmol) in THF (120 ml) was added dropwise at 0° C., the mixture was stirred for 4 hours at room temperature, water (180 ml) was added, the suspension was filtered and dried under ambient conditions to yield 6.01 g. The filtrate was extracted three times with dichloromethane (3×90 ml), the combined organic layers were dried over sodium sulfate and evaporated to yield 6.75 g.

$^1$H NMR (400 MHz, DMSO-d$_6$) d ppm 3.74 (s, 6 H) 5.04-5.11 (s, 4 H) 6.84 (s, 4 H)

$^{13}$C NMR (100 MHz, DMSO-d$_6$) d ppm 31.3, 52.8, 67.2, 132.6, 134.5, 164.0, 165.1, 197.6

Synthesis of (E)-But-2-enedioic acid 2-hydroxy-3-((E)-3-methoxycarbonyl-acryloyloxy)-propyl ester methyl ester

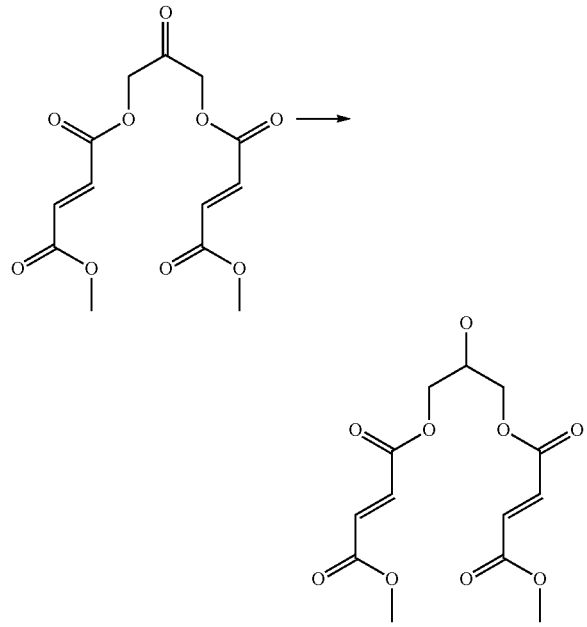

To a solution of (E)-But-2-enedioic acid 3-((E)-3-methoxycarbonyl-acryloyloxy)-2-oxo-propyl ester methyl ester (10 g; 34.94 mmol) in THF (330 ml) were added sodium triacetoxy borohydride (12.96 g; 61.1 mmol) and glacial acetic acid (4 ml) at room temperature under vigorous stirring. The mixture was stirred at room temperature overnight. Water (100 ml) and ethylacetate (400 ml) were added and the organic phase was separated, the water layer was extracted twice with ethylacetate (1×350 ml and 1×250 ml). The combined organic layers were washed twice with water (2×400 ml), dried over sodium sulfate and evaporated to yield 9.27 g as a white solid. The solid was dissolved in acetone (90 ml) at room temperature and filtrated through a pad of silica (5.5×3 cm), the silica pad was washed with acetone (2×100 ml). The combined organic layers were evaporated to yield 7.82 g. The solid was suspended in diethylether (75 ml) and stirred at room temperature overnight. The product was filtrated off and dried under ambient conditions to yield 6.07 g.

Example 8

Investigation and Comparison of the Kinetics of MMF-Release of the Different Compounds of the Present Invention and DMF During Incubation in Intestinal Fluid of the Minipig 1. Materials
1.1 Test Compounds
Compounds of the present invention were synthesized as described above.
1.2 Intestinal Fluid
Intestinal fluid samples were prepared at CiToxLAB Scantox A/S. The samples were taken from 1 female Gottingen SPF minipig from CiToxLAB Scantox A/S standard stock, originally obtained from Ellegaard Gottingen Minipigs A/S, DK-4261 Dalmose, Denmark. The minipig was 10 months old and the body weight was 21 kg. The minipig was identified by an individual number tagged to the pinna of one ear (animal number is documented in the raw data).

The minipig was fasted for approximately 28 hours before sampling of intestinal fluid. On the day of sampling, the minipig was weighed and anaesthetised by an intramuscular injection in the neck or in the left hind leg (about 0.3 ml per kg body weight) of a mixture of Zoletil 50 Vet., Virbac, France (125 mg tiletamine and 125 mg zolazepam), Rompun Vet., Bayer, Germany (20 mg xylazine/ml, 6.5 ml), Ketaminol Vet., Veterinaria AG, Switzerland (100 mg ketamine/ml, 1.5 ml) and Methadon DAK, Nycomed Danmark, Denmark (10 mg methadon/ml, 2.5 ml).

Intestinal fluid was obtained by flushing one jejunal segment, measuring 30.2 cm, with saline. Intestinal fluid together with saline used for flushing was placed in centrifuge tubes. All samples were frozen at −70° C. and shipped on dry ice to the Sponsor for further use.

Example 9

In Vivo Pharmacology

The pharmacological efficacy was investigated in experimental autoimmune encephalomyelitis (EAE) in the mouse.

The experiments were performed as follows: male C57BL/6 mice, 12 weeks old, 10 animals per treatment group, were used. On day 1, animals were immunized by sub-cutaneous injection of MOG35-55, which was mixed in complete Freund's adjuvants. On the same day as well as on day 3 the animals received a sub-cutaneous injection of Pertussis-toxin.

Assessment and comparison of the efficacy of compounds of the invention and DMF (reference) in MOG35-55-induced experimental autoimmune encephalomyelitis (EAE) in C57BL/6 mice.

Figure 2:
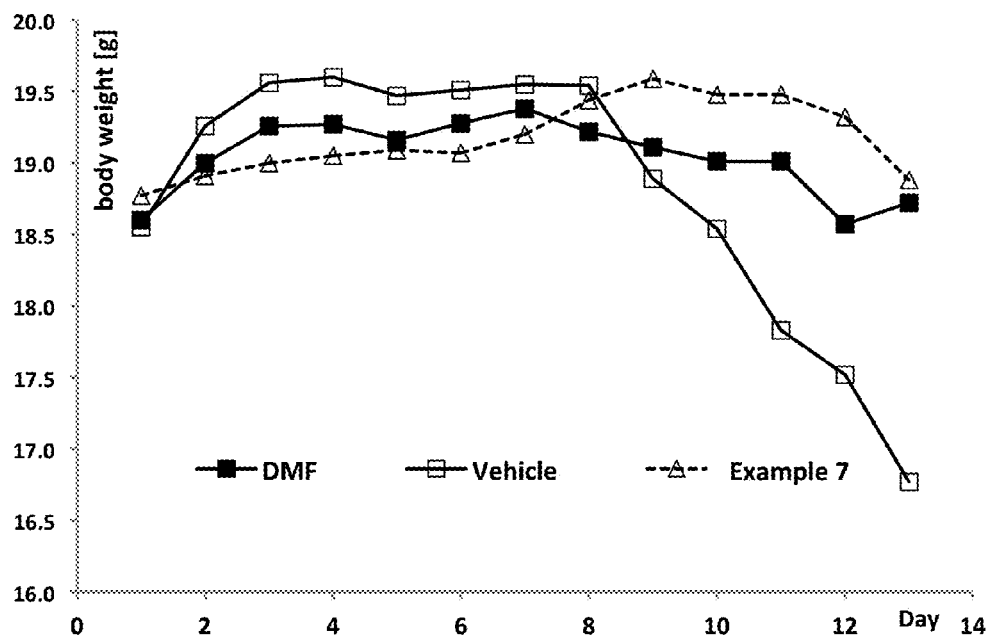
FIG. 2 shows body weight results.
Figure 3:
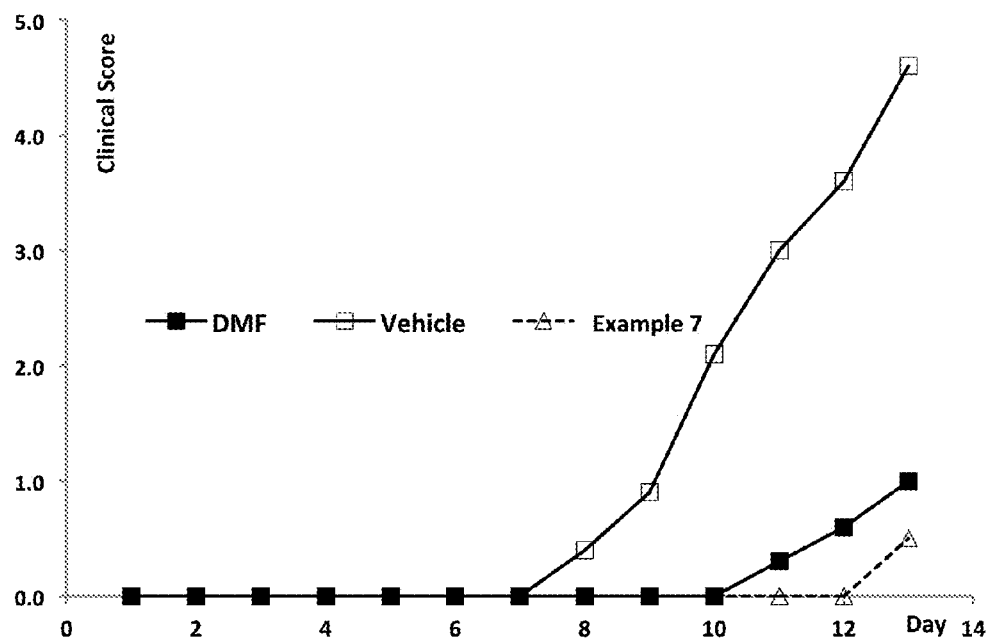
FIG. 3 shows clinical score results.

Test system: male C57BL/6 mice, 12 weeks old; 10 animals per treatment group;
Induction of EAE: Day 1—subcutaneous injection of MOG35-55, suspended in complete Freund's adjuvants and intraperitoneal injection of pertussis toxin.
Day 3—intraperitoneal injection of pertussis toxin.
Treatment: Dimethylfumarate and test substances or vehicle only were administered via oral and intravenous route. For oral administration, test substances were dissolved or suspended in 0.5% hydroxyethylcellulose (dissolved in 50 mM potassium dihydrogenphosphate, pH 5.0). Drug concentration in dose formulations: 11.54 mM;
Dose volume: 10 ml/kg body weight;
Start of treatment: Day 1
Observations (clinical Observations were recorded daily between day 1 and 13. score and body weight):
Clinical score: grade 0-10; 0 (no impairments), 1 (normal movement; limp tail: proximal ⅔of the tail is limp and droopy), 2 (normal movement; whole tail is limp); 3 (wobbly walk; absent righting reflex), 4 (gait ataxia), 5 (mildparaparesis), 6 (moderate paraparesis), 7 (severe paraparesis or paraplegia), 8 (tetraparesis), 9 (moribund), 10 (death).
Result
The results are shown in FIG. 2 (body weight) and FIG. 3 (clinical score). With treatment of animals with vehicle only, first symptoms were observed on day 8 (3 of 10 animals; mean clinical score: 0.4) and the status worsened until day 13 (all animals affected; clinical score: 4.6). In contrast, the prophylactic treatment of animals with DMF or compound of Example 7 protected from the development of clinical symptoms and the body weight remained stable.

Example 10

Membrane Permeability

The membrane permeability was investigated in Caco-2 monolayers. DMF was investigated in a separate experiment for comparison.

Based on the assumption that in vivo, the intact molecules will be pre-systemically metabolized, the permeability test was performed only in the apical→basolateral direction. The test concentration in the apical medium was 250 µM. The assay was validated by controlling the membrane integrity with Lucifer yellow (post-experimental integrity) and by determination of the permeability of atenolol (low permeability), testosterone (high permeability) and erythromycin (P-gp substrate). Furthermore, a significant metabolism or degradation of the test compound was expected and therefore the parent compound as well as MMF was determined in the acceptor compartment (basolateral medium). Sampling time points were 15, 45 and 90 min.

The results are summarized the following:

| Item | Direction | Papp × 10$^{-6}$ [cm/sec] mean ± s.d. (CV) | Recovery [%] mean ± s.d. (CV) | Efflux ratio (b-a/a-b) |
|---|---|---|---|---|
| Atenolol | a-b | 0.3 ± 0.1 (45.5%) | 104.1 ± 3.1 (3.0%) | 2.7 |
|  | b-a | 0.8 ± 0.2 (23.6%) | 103.3 ± 5.5 (5.3%) |  |
| Erythromycin | a-b | 0.1 ± 0.2 (161.8%) | 91.0 ± 1.9 (2.1%) | 100.8 |
|  | b-a | 12.3 ± 0.4 (2.9%) | 99.9 ± 2.4 (2.4%) |  |
| Testosterone | a-b | 18.2 ± 2.2 (11.9%) | 67.3 ± 1.2 (1.8%) | 2.7 |
|  | b-a | 49.5 ± 1.3 (2.7%) | 94.9 ± 0.9 (0.9%) |  |
| Example 7 | a-b | 2.5 ± 0.2 (8.4%) | 18.3 ± 1.3 (7.1%) | N/A |
| Atenolol | a-b | 0.3 ± 0.1 (30.0%) | 101.6 ± 3.2 (3.1%) | 2.8 |
|  | b-a | 1.0 ± 0.1 (9.2%) | 95.0 ± 5.3 (5.5%) |  |
| Erythromycin | a-b | 0.2 ± 0.02 (12.0%) | 107.7 ± 2.2 (2.1%) | 55.9 |
|  | b-a | 11.5 ± 0.5 (4.0%) | 89.1 ± 8.5 (9.5%) |  |
| Testosterone | a-b | 16.2 ± 1.6 (9.8%) | 62.5 ± 2.1 (3.4%) | 1.9 |
|  | b-a | 30.7 ± 1.7 (5.7%) | 76.1 ± 4.5 (6.0%) |  |
| DMF | a-b | 1.8 ± 0.2 (12.3%) | 11.6 ± 1.0 (8.2%) | N/A |

The mean apparent permeability of the test compounds expressed as $P_{app} \times 10^{-6}$ are 1.8±0.2 cm/sec for DMF and 2.5±0.2 cm/sec for Example 7. Compared to the reference molecules, DMF and the MMF-prodrug of Example 7 can be categorized as moderate permeability drugs. The recovery of all test and reference compounds was similar (11.6% for DMF, 18.3% for Example 7) which indicates a similar susceptibility to hydrolysis.

Example 11

In Vivo Pharmacokinetics

The pharmacokinetics of MMF after administration of Example 7 and DMF for comparison was investigated in female NMRI mice (3 animals per group). The test compound was dissolved in DMSO/PEG300 (20/80) and administered p.o. (gavage) at a dose volume of 10 ml/kg. DMF was given at a dose of 45 mg/kg. The test compound was dosed at a MMF-equivalent dose, i.e. 49.4 mg/kg. Blood samples were taken at 0.25, 0.5, 1.0, 2.0, 4.0, 6.0 and 8.0 h after drug administration.

Figure 4:
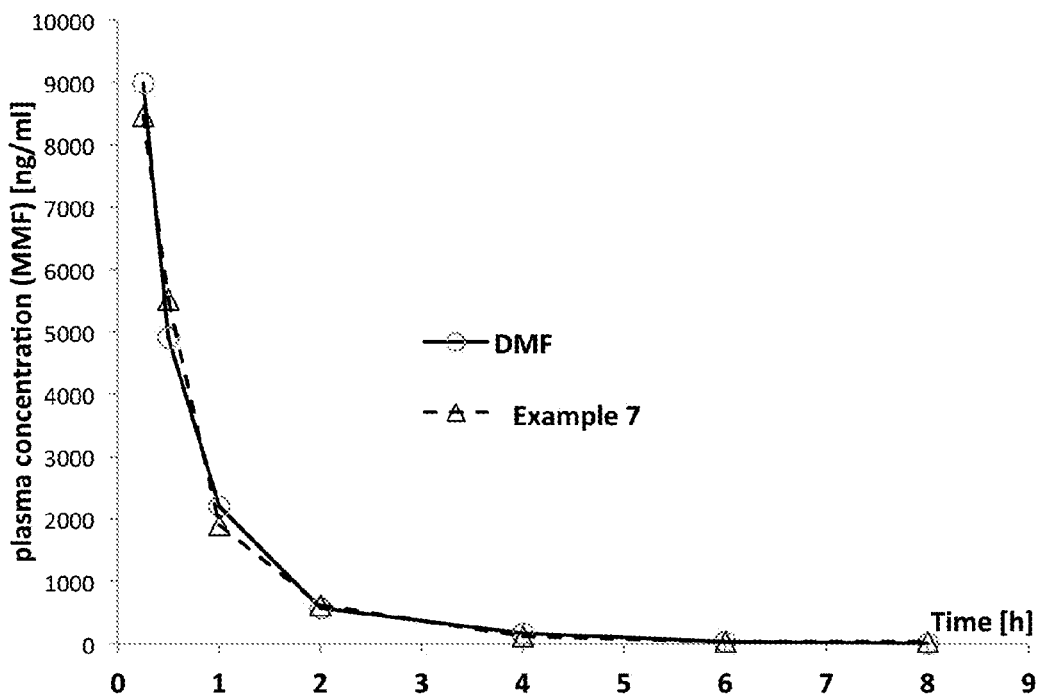
FIG. 4 shows mean concentration vs. time profiles of MMF in linear scale.
Figure 5:
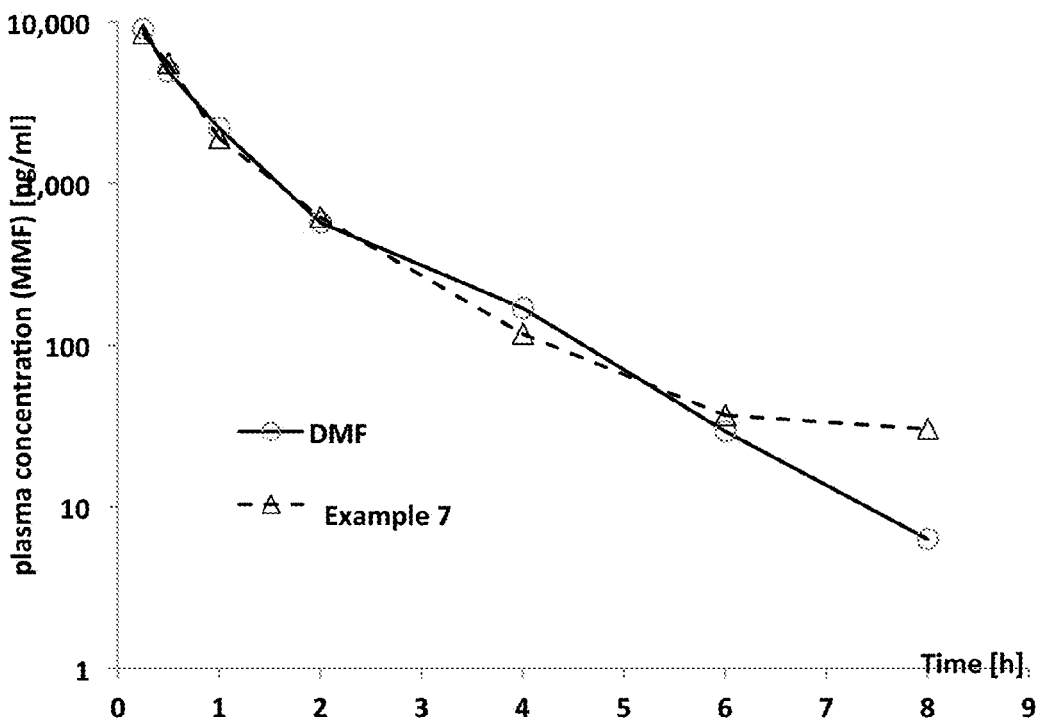
FIG. 5 shows mean concentration vs. time profiles of MMF in semi-logarithmic scale.

Mean concentration vs. time profiles of MMF in the linear and semi-logarithmic scale are shown in FIG. 4 and FIG. 5.

Pharmacokinetic parameters, derived by non-compartmental analysis for test compound Example 7

| Animal no. | $C_{max}$ [ng/ml] | $T_{max}$ [h] | $AUC_{last}$ [ng*h/ml] | $t_{1/2}$ [h] | $AUC_{inf}$ [ng*h/ml] | $AUC_{\%Extrap}$ [%] | F* [%] |
|---|---|---|---|---|---|---|---|
| 109 | 8.820 | 0.25 | 6.730 | 1.08 | 6.770 | 0.56 | 96.3 |
| 110 | 8.070 | 0.25 | 6.680 | 0.71 | 6.690 | 0.18 | 95.2 |
| 111-112 | 8.500 | 0.25 | 7.180 | 1.41 | 7.370 | 2.50 | 105 |
| mean: | 8.463 | 0.25 | 6.863 | 1.07 | 6.943 | 1.08 | 99 |
| s.d.: | 376 | 0.00 | 275 | 0.35 | 372 | 1.24 | 5 |
| C.V.: | 4% | 0% | 4% | 33% | 5% | 115% | 5% |

*F = bioavailability of MMF relative to administration of DMF and of DMF for comparison:

| Animal no. | $C_{max}$ [ng/ml] | $T_{max}$ [h] | $AUC_{last}$ [ng*h/ml] | $t_{1/2}$ [h] | $AUC_{inf}$ [ng*h/ml] | $AUC_{\%Extrap}$ [%] | F [%] |
|---|---|---|---|---|---|---|---|
| 101 | 13.000 | 0.25 | 6.750 | 1.13 | 6.800 | 0.79 | N/A |
| 102 | 7.330 | 0.25 | 7.630 | 2.83 | 7.710 | 1.00 | N/A |
| 103-104 | 6.640 | 0.25 | 6.530 | 0.96 | 6.580 | 0.81 | N/A |
| mean: | 8.990 | 0.25 | 6.970 | 1.64 | 7.030 | 0.87 | N/A |
| s.d.: | 3.490 | 0.00 | 582 | 1.03 | 599 | 0.12 | N/A |
| C.V.: | 39% | 0% | 8% | 63% | 9% | 14% | N/A |

The rate and extent of systemic exposure of animals to MMF after administration of the different compounds was very similar. Compared to the bioavailability of MMF after administration of DMF, the relative bioavailability of MMF after administration of test compound (Example 7) was 99%.

1. Analytical Methods
1.1. Quantification of MMF by LC-MS
1.1.1. Analytical Instrument
Instrument: Acquity UPLC system coupled with a TQ detector (triple quadruple mass spectrometer)
UPLC method:
Column: Phenomenex Kinetex C18, 100A, 2.6 µm (150×4.6 mm)
flow: 0.4 ml/min
split: appr. 100 µl/min to MS
Temperature: 30° C.
solvent system (isocratic):
  Solvent A 25% water with 0.1% acetic acid
  Solvent B 75% methanol with 0.1% acetic acid
stoptime: 6 min
autosampler temperature: 8° C.
injection volume: 4 µl
retention time: MMF: 4.3 min
  MEF: 4.7 min
Mass Spectrometry
software: Masslynx 4.1
detection mode: electrospray/negative ions (ESP−)
capillary voltage: 2.3 kV
source temperature: 100° C.

desolvation temperature: 450° C.
cone voltage: 18 V
desolvation gas: N$_2$, 650 L/h
cone gas: N$_2$, 20 L/h
collision gas: argon, appr. 3.3*10$^{-3}$ mbar
collision energy: 11 eV
MRM [m/z]: 128.94>85.03 Monomethylfumarate dwell:200 msec
142.99>99.06 Monoethylfumarate (ISTD) dwell:200 msec 1.1.2. Stock and Calibration Solutions Stock (SS), working (WS) and calibration solutions of the analyte monomethyl fumarate (MMF) and the internal standard (ISTD) monomethyl fumarate (MEF) were prepared as described below.

SS$_{MMF}$: In a 10 ml volumetric flask, 6.5 mg MMF (Batch: MKRJ0642V/Aldrich) were dissolved in methanol and made up to volume (c=650 μg/ml)

SS$_{ISTD}$: In a 100 ml volumetric flask, 10 mg MEF (Batch: STBC5219V/Aldrich) were dissolved in methanol and made up to volume (c=100 μg/ml)

WS$_{ISTD}$: 100 μl SSISTD were transferred into a 10 ml volumetric flask and made up to volume with acetonitrile (c=1,000 ng/ml);

Calibration solutions were prepared by serial dilution of SS$_{MMF}$; diluted small intestinal fluid (diluted by 1/20 v/v with 50 mM KH$_2$PO$_4$, pH 6.8; (dil IF) was used as matrix. The dilution scheme is given below:

| calibration solution | Preparation | | Concentration | |
|---|---|---|---|---|
| | | | [ng/ml] | [μM] |
| cal6500 | 8 μl SS$_{MMF}$ | +792 μl dil IF | 6,500 | 50 |
| cal3250 | 50 μl cal6500 | +50 μl dil IF | 3250 | 25 |
| cal650 | 20 μl cal6500 | +180 μl dil IF | 650 | 5.0 |
| cal 325 | 50 μl cal650 | +50 μl dil IF | 325 | 2.5 |
| cal65 | 10 μl cal650 | +90 μl dil IF | 65 | 0.5 |

1.1.3. Sample Preparation

50 μl sample (calibration solution or sample of an incubation experiment with MMF prodrugs) was mixed with 50 μl WS$_{ISTD}$, 20 μl formic acid and 100 μl acetonitrile. This mixture was vortexed for 15 sec and centrifuged (13,000 rpm, 3 min). Thereafter, 4 μl of the supernatant were subjected to LC-MS analysis.

1.2. Incubation Experiments with DMF (Reference) and Compounds of the Invention 1.2.1. Stock Solutions Stock solutions were prepared in DMSO or, for one compound, in DMSO with 10% (v/v) water. Concentrations in stock solutions were 5.00, 2.50 and 1.67 mmol for compounds with one, two and three molar MMF equivalents.

| Compound | MW | Sample weight [mg] | dissolved in | Concentration [mg/ml] | [mmol] |
|---|---|---|---|---|---|
| DMF | 144.13 | 7.21 | 10 ml DMSO | 0.721 | 5.00 |
| Example 7 | 316.27 | 3.96 | 5 ml DMSO | 0.792 | 2.50 |

1.2.2. Incubation Experiment

In a HPLC glass vial, 8 μl of stock solution were mixed with 792 μl dil IF and the mixture was stirred (250 rpm) in a water bath (T=37° C.).

Immediately after mixing as well as at t=15 min, 30 min, 60 min, 90 min and 120 min, 50 μl were withdrawn and prepared for LC-MS analysis as described in chapter. 2.1.3.

Incubations were continued and in case the result of analysis of the 120 min indicated the presence of remaining intact MMF prodrug, additional samples were taken (t=360 or 420 min and at 1,260 or 1,320 min) and analysed.

2. Results 2.1. Calibration of the Analytical Method

Each calibration solution was analysed two-fold. The second analysis was carried out approx. 18 h after storage of the sample in the autosampler, which was cooled to 8° C. The results demonstrate that the ratio of peak area remains essentially unchanged between the first and the second analysis.

The concentration/peak area ratio data pairs were subjected to regression analysis with 1/x weighting and the resulting calibration equation was used to quantify the MMF content in incubation samples.

| calibration standard | nominal concentration [ng/ml] | Analysis | area/area(ISTD) | mean | RSD |
|---|---|---|---|---|---|
| cal6500 | 6,500 | 1$^{st}$ analysis | 3.569 | 3.567 | 0.07 |
| | | 2$^{nd}$ analysis | 3.564 | | |
| cal3250 | 3,250 | 1$^{st}$ analysis | 1.710 | 1.681 | 1.73 |
| | | 2$^{nd}$ analysis | 1.652 | | |
| cal650 | 650 | 1$^{st}$ analysis | 0.348 | 0.347 | 0.29 |
| | | 2$^{nd}$ analysis | 0.346 | | |
| cal325 | 325 | 1$^{st}$ analysis | 0.174 | 0.169 | 2.96 |
| | | 2$^{nd}$ analysis | 0.164 | | |
| cal65 | 65 | 1$^{st}$ analysis | 0.036 | 0.035 | 2.86 |
| | | 2$^{nd}$ analysis | 0.034 | | |
| cal0 | 0 | 1$^{st}$ analysis | 0.000 | 0.000 | 0.00 |
| | | 2$^{nd}$ analysis | 0.000 | | |

As can be seen from FIG. 1 the inventive compounds according to Formula (II) show a significantly slower hydrolyzation to MMF than DMF.

The invention claimed is:

1. A compound according to one of Formula (II) or Formula (IIa):

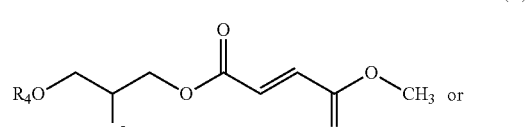

Formula (II)

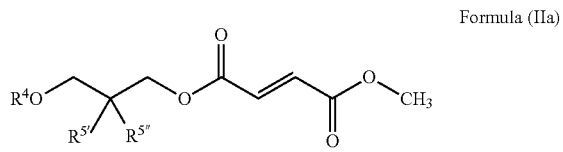

Formula (IIa)

wherein R$^4$ is trans —CO—CH=CH—COOCH$_3$;

R$^5$ is —(CH$_2$)$_n$—COR$^{51}$ or —(CH$_2$)$_n$—OH with n being 0, 1 or 2, wherein R$^{51}$ is —OR$^{52}$ or NR$^{53}$R$^{54}$ wherein R$^{52}$, R$^{53}$ and R$^{54}$ are independently hydrogen or alkyl with 1 to 4 carbon atoms;

R$^{5'}$ and R$^{5''}$ taken together are =O, =S or NR$^{100}$, wherein R$^{100}$ is hydrogen or alkyl with 1 to 4 carbon atoms.

2. Compound according to claim 1, wherein in Formula (II) $R^5$ is —$(CH_2)_n$—OH with n being 0, 1 or 2.

3. Compound according to claim 1, wherein the compound according to Formula (II) is the compound according to of Formula (VII)

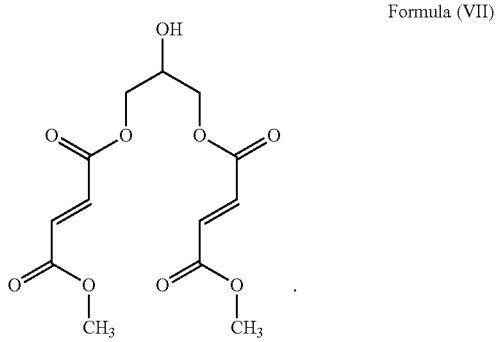 [SMILES: COC(=O)/C=C/C(=O)OCC(O)COC(=O)/C=C/C(=O)OC]

Formula (VII)

4. Pharmaceutical composition comprising a compound according to claim 1.

5. Pharmaceutical composition according to claim 4 comprising
   (i) 0.01 to 10 mmol of the compound; and
   (ii) optionally pharmaceutical excipients.

6. Pharmaceutical composition according to claim 4, wherein the composition is a solid oral dosage form.

7. Pharmaceutical composition according to claim 4, wherein an in-vitro drug release after 2 hours is less than 10%, measured according to USP, Apparatus II, paddle, 0.1 HCl, 37° C., 50 rpm.

8. Is subject in need thereof a therapeutically effective amount of a compound according to claim 1.

* * * * *